(12) United States Patent
Lewis et al.

(10) Patent No.: US 9,789,213 B2
(45) Date of Patent: Oct. 17, 2017

(54) EGFL7 TARGETING AND/OR BINDING POLYPEPTIDES AND METHODS FOR INHIBITING ANGIOGENESIS

(71) Applicant: LONDON HEALTH SCIENCES CENTRE RESEARCH INC., London (CA)

(72) Inventors: John Lewis, Edmonton (CA); Choi-Fong Cho, Guelph (CA); Leonard Luyt, London (CA)

(73) Assignee: LONDON HEALTH SCIENCES CENTRE RESEARCH INC., London (CA)

( * ) Notice: Subject to any disclaimer, the term of this patent is extended or adjusted under 35 U.S.C. 154(b) by 0 days.

(21) Appl. No.: 14/388,678

(22) PCT Filed: Mar. 15, 2013

(86) PCT No.: PCT/CA2013/000251
§ 371 (c)(1),
(2) Date: Sep. 26, 2014

(87) PCT Pub. No.: WO2013/142961
PCT Pub. Date: Oct. 3, 2013

(65) Prior Publication Data
US 2015/0071855 A1    Mar. 12, 2015

Related U.S. Application Data

(60) Provisional application No. 61/616,131, filed on Mar. 27, 2012.

(51) Int. Cl.
| | |
|---|---|
| *A61K 51/08* | (2006.01) |
| *C07K 7/06* | (2006.01) |
| *C07K 7/08* | (2006.01) |
| *C07K 14/485* | (2006.01) |
| *A61K 49/00* | (2006.01) |
| *C07K 16/22* | (2006.01) |
| *C12N 15/113* | (2010.01) |
| *C07K 14/47* | (2006.01) |
| *A61K 38/00* | (2006.01) |

(52) U.S. Cl.
CPC ........ *A61K 51/088* (2013.01); *A61K 49/0043* (2013.01); *A61K 49/0056* (2013.01); *C07K 7/06* (2013.01); *C07K 7/08* (2013.01); *C07K 14/4703* (2013.01); *C07K 14/485* (2013.01); *C07K 16/22* (2013.01); *C12N 15/1136* (2013.01); *A61K 38/00* (2013.01); *C12N 2310/14* (2013.01)

(58) Field of Classification Search
CPC .................. A61K 51/088; C07K 7/06
See application file for complete search history.

(56) References Cited

U.S. PATENT DOCUMENTS

| | | | |
|---|---|---|---|
| 7,947,278 B2 | 5/2011 | Kuo et al. | |
| 2005/0255114 A1 | 11/2005 | Labat et al. | |
| 2007/0031437 A1 | 2/2007 | Filvaroff et al. | |
| 2009/0297512 A1 | 12/2009 | Filvaroff et al. | |
| 2010/0203041 A1* | 8/2010 | Ye .......................... | C07K 16/22 424/133.1 |
| 2010/0285009 A1* | 11/2010 | Ye .......................... | C07K 16/22 424/133.1 |

FOREIGN PATENT DOCUMENTS

| | | |
|---|---|---|
| WO | WO 98/57983 | 12/1998 |
| WO | WO 2008/010986 A2 | 1/2008 |

OTHER PUBLICATIONS

European Search Report Corresponding to PCT/CA2013000251; dated Oct. 20, 2015.
Lelievre et al., Etienne, "VE-statin/egfl7 regulates vascular elastogenesis by interacting with lysyl oxidases", vol. 27, Jan. 1, 2008, pp. 1658-1670, retrieved from the internet on Sep. 22, 2015 at http://emboi.embopress.org/content/27/12/1658.full.pdf.
Nichol, et al., "Impaied angiogenesis and altered Notch signaling in mice overexpressing endothelial Egfl7", *Blood*, vol. 116, No. 26, Dec. 23, 2010, pp. 6122-6143.
Schmidt, et al., Mirko H., "Epidermal growth factor-like domain 7 (EGFL7) modulates Notch signaling and affects neural stem cell renewal", *Nature Cell Biology*, vol. 11, No. 7, Jun. 7, 2009 pp. 873-880.
GenBank Database, Accession No: ACM37363, Apr. 15, 2009 (see amino acids 306-317).
GenBank Database, Accession No: ACT90373, Jan. 14, 2010 (see amino acids 2-10).
International Search Report and Written Opinion Corresponding to International Application No. PCT/CA2013/000251; dated Jul. 25, 2013.
European Office Action for European Patent Application No. 13768944.4, corresponding to PCT/CA2013/000261, dated Jun. 10, 2016, 4 pages.

* cited by examiner

*Primary Examiner* — Amber D Steele
(74) *Attorney, Agent, or Firm* — Myers Bigel, P.A.

(57) ABSTRACT

Polypeptides that target and/or bind to EGFL7 or its receptor and thereby reduce EGFL7 pro-angiogenic activity are provided. In this way, the polypeptides are, in an aspect, useful in the treatment of diseases, disorders, or conditions that involve pathological angiogenesis, such as, for example, cancer.

20 Claims, 14 Drawing Sheets

```
  1 ---MRGSQEVLLMWLLVLAVGGT-EHAYRPGRRVCAVRAHG---DPVSES  43  human
  1 MQTMWGSGELLVAWFLVLAADGTTEHVYRPSRRVCTVGISG---GSISET  47  mouse
  1 -MWKVSCLVTGYLLILAVTSAAAD-HLYRTGRRICSADGHPG-TVSVTQS  47  xenopus*
  1 ---MYTALLLSSSLFELHVTC-TPQTHSHHGRRVGVGDVWSRRVSYSTES  46  zebrafish 44 VQRVYQPFLFTCDGHRACSTYRTIYRTAYRRSPGLAPARPRYA-CCPGW   92  human
 48 VQRVYQPYLJTCDGHRACSTYRTIYRTAYRRSPGVTPARPRYA-CCPGW   96  mouse
 48 VQPVHSPIMTLCEGHRICSTYRTTYKVSYRQVS-RKTSFPLYS-CCPGW   95  xenopus*
 47 LQPVHKPYITMGQNHRMCSTYKTIYKVSYRQVTRAAPNLQIYPECCPGW   96  zebrafish 93 KRTSGLPGACGAAICQPPCRNGGSCVQPGRCRCPAGWRGDTCQSDVDECS 142  human
 97 KRTSGLPGACGAAICQPPCGNGGSCIRPGHCRCPVGWQGDTCQTDVDECS 146  mouse
 96 RRIGAQTHSCGQALCRLQCQNGGTCVSSNKCECPAGWRGIHCQMDVDECS 145  xenopus*
 97 RR-MH-SHNCNQAVCEQSCANGGSCVRPNHCACLRGWTGRFCQIDVDECK 144  zebrafish 143 ARRGGCPQRCINTAGSYWCQCWEGHSLSADGTLCVPKGGPPRVAPNPT-- 191  human
147 TGEASCPQRCVNTVGSYWCQGWEGQSPSADGTRCLSKEGPSPVAPNPTA- 196  mouse
146 DGTHQCSQACINSAGSFSCECLEGYRLMADGKTCRKVPAPTVPPASPTSV 195  xenopus*
145 EAQH-CSQKCVNTLGSFQCVCEEGFSLDEDKVTCSKNPASSRNTGGG--- 192  zebrafish 192 ---GVDSAMKEEVQRLQSRVDLLEEKLQLVLAPLHSLASQALEHG----L 233  human
197 ---GVDSMAREEVYRLQARVDVLEQKLQLVLAPLHSLASRSTEHG----L 238  mouse
196 QESGIPHSVKEEMAELRSKIDVLEQKLHLLLTPFQGLTTFSPDD-----A 240  xenopus*
193 --LGLVENVTEEVQILKNRVELLEQKLEMVLAPFTTLLPLDGAGDTNSFL 238  zebrafish 234 PDPGSLLVHSFQQLGRIDSLSEQISFLEEQLGSCSCKKDS 273  human     (SEQ ID NO:1)
239 QDPGSLLAHSFQQLDRIDSLSEQVSFLEEHLGSCSCKKDL 278  mouse     (SEQ ID NO:2)
241 ADPIALCTRSLQQLDRIDSLSEQISFLEERLETCSCKTEL 280  xenopus*  (SEQ ID NO:3)
239 SERTNFLSHSLQQLDRIESLSEQVGFLEERIGAGGCQEN- 277  zebrafish (SEQ ID NO:4)
```

Figure 8

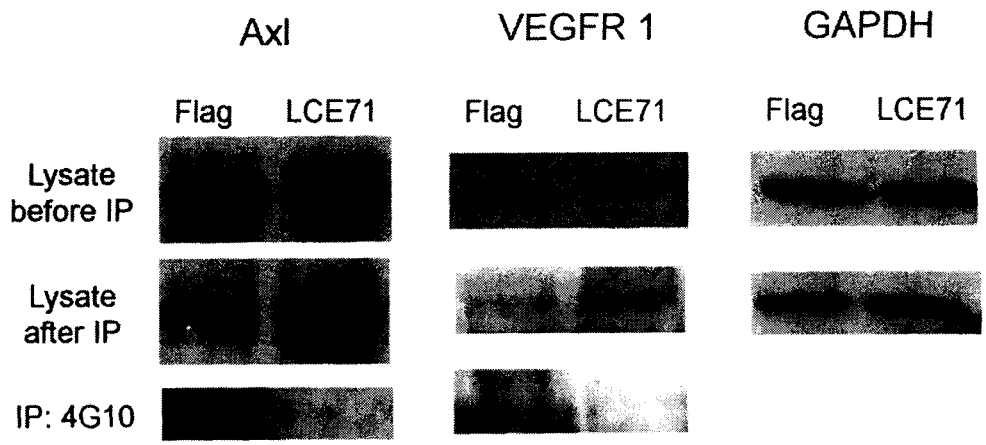
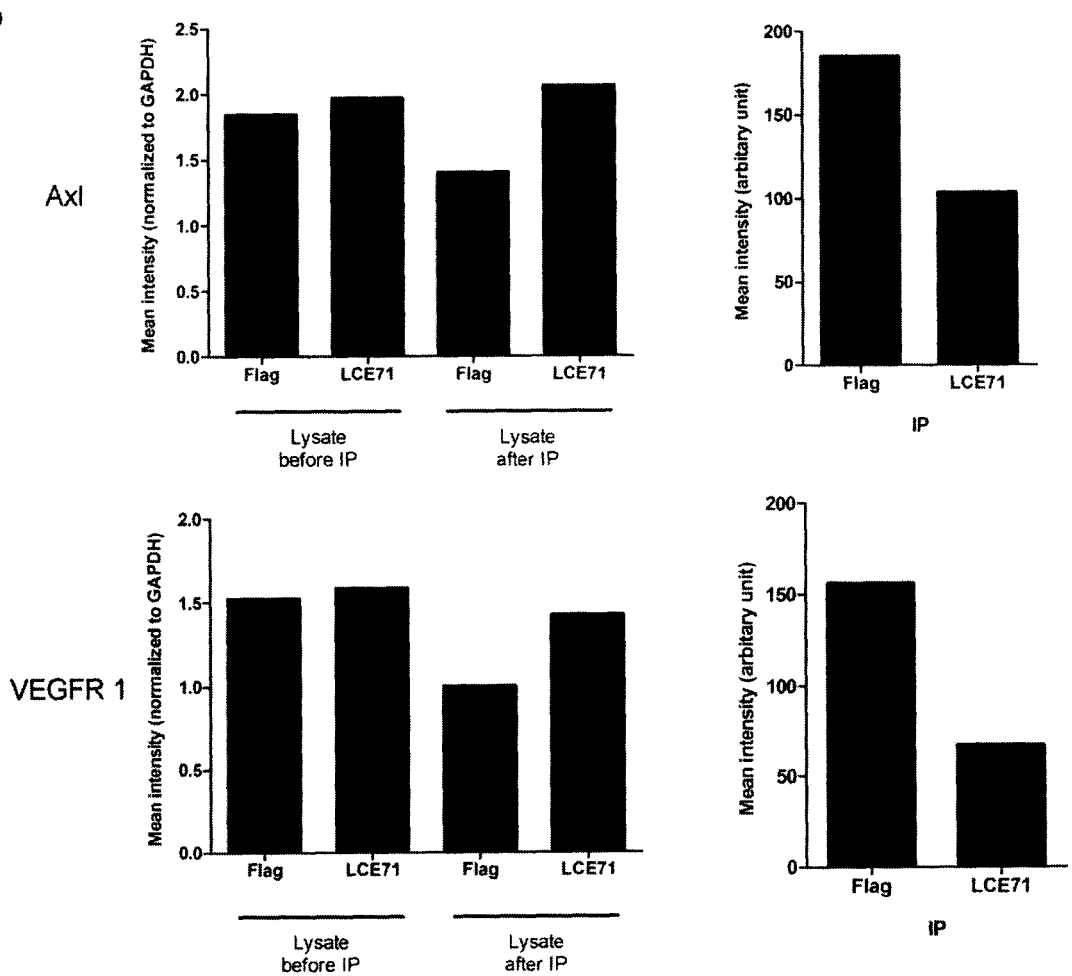
Figure 12

EGFL7 TARGETING AND/OR BINDING POLYPEPTIDES AND METHODS FOR INHIBITING ANGIOGENESIS

STATEMENT OF PRIORITY

This application is a 35 U.S.C. §371 national phase application of International Application Serial No. PCT/CA2013/000251, filed Mar. 15, 2013, which claims the benefit, under 35 U.S.C. §119(e), of U.S. Provisional Application No. 61/616,131, filed Mar. 27, 2012, the entire contents of each of which are incorporated by reference herein.

STATEMENT REGARDING ELECTRONIC FILING OF A SEQUENCE LISTING

A Sequence Listing in ASCII text format, submitted under 37 C.F.R. §1.821, entitled 3477-122TS_ST25.txt, 18,338 bytes in size, generated on Oct. 29, 2014 and filed via EFS-Web, is provided in lieu of a paper copy. This Sequence Listing is incorporated herein by reference into the specification for its disclosures.

FIELD OF THE INVENTION

The present invention relates to angiogenesis. More specifically, the present invention is concerned with EGF-like domain 7 (EGFL-7) interacting polypeptides and methods of using such polypeptides for inhibiting angiogenesis, as well as methods for the treatment, diagnosis, and imaging of conditions that involve pathological angiogenesis.

BACKGROUND OF THE INVENTION

Development of a vascular supply is a fundamental requirement for many physiological and pathological processes, particularly in actively growing tissues such as embryos and tumours. Such tissues satisfy a need for adequate blood supply by producing pro-angiogenic factors, which promote new blood vessel formation through a complex but orderly event known as angiogenesis. In the case of tumour growth, angiogenesis is believed to be crucial for the transition from hyperplasia to neoplasia and for providing nourishment for the growth and metastasis of the tumour. Thus, angiogenesis allows the tumour to grow beyond about 1 mm in diameter and also allows provides routes for the dissemination and subsequent recolonization of metastatic tumour cells.

Therefore, angiogenesis is emerging as an important biomarker and therapeutic target in cancer. While the majority of current non-invasive vascular imaging approaches can estimate vessel density, a recent comprehensive analysis of tumour vasculature in prostate cancers concluded that microvessel density is not linked to cancer-specific mortality after adjusting for clinical factors. The shape and size of vessels, however, is highly predictive and men with the most irregularly shaped vessels being 17.1 times more likely to develop lethal disease (Mucci et al., 2009, J Clin Oncol, 27:5627-33).

The process of vascular development is tightly regulated. To date, a significant number of molecules, mostly secreted factors produced by surrounding cells, have been shown to regulate endothelial cell differentiation, proliferation, migration and coalescence into cord-like structures. For example, vascular endothelial growth factor (VEGF) has been identified as a key factor involved in stimulating angiogenesis and in inducing vascular permeability. Anti-VEGF monoclonal antibodies or other inhibitors of VEGF action are promising candidates for the treatment of tumours and various intraocular neovascular disorders. Such antibodies are described, for example, in EP 817,648, WO 1998/45331, and WO 1998/45332.

In addition, an extracellular matrix (ECM)-associated protein designated epidermal growth factor-like 7 (EGFL7) has been shown to be expressed by endothelial cells and to have a role in angiogenesis (Parker et al., 2004, Nature, 428:754-758; Nichol and Stuhlmann, 2012, 119:1345-1352). While some have suggested the use of inhibitory anti-EGFL7 monoclonal antibodies for the treatment of tumours (U.S. 2007/0031437, U.S. 2009/0297512, U.S. 2010/0203041, and U.S. 2010/0285009), others have suggested the use of agonists of EGFL7 to enhance the activity of EGFL7 for the treatment of tumours (U.S. Pat. No. 7,947,278).

There is still a need for alternative imaging approaches that can aid in estimating vessel shape and size and to identify different approaches for targeting EGFL7.

SUMMARY OF THE INVENTION

The present invention relates, in aspects, to polypeptides that target and/or bind to EGFL7 or its receptor and thereby reduce EGFL7 pro-angiogenic activity. In this way, the polypeptides are, in an aspect, useful in the treatment of diseases, disorders, or conditions that involve pathological angiogenesis, such as, for example, cancer.

EGFL7 is specifically expressed in endothelium that is undergoing active angiogenesis. Therefore, polypeptides that bind to or interact with EGFL7 also find use, in an aspect, in methods of imaging subjects afflicted with pathological angiogenesis. In another aspect, such polypeptides are also useful as targeting moieties for targeted anti-angiogenic therapy. By attaching the polypeptides described herein directly or indirectly to a pharmaceutical agent, the polypeptides are capable of aiding in delivering the pharmaceutical agent to an area of active angiogenesis, thus targeting the pharmaceutical agent to the desired region The presence of EGFL7 in a tumour may also be predictive of prognosis and, accordingly, the polypeptides described herein are also useful, in another aspect, in methods of predicting prognosis in a subject afflicted with cancer. The polypeptides described herein also find use, in aspects, in methods of screening for and/or diagnosing cancer or other diseases, disorders, or conditions involving pathological angiogenesis.

In accordance with an aspect, there is provided a polypeptide that interacts with a domain of EGFL7.

In an aspect, the polypeptide interacts with the C-terminal domain of EGFL7, or wherein the polypeptide interacts with EGFL7 outside of the Notch binding domain of EGFL7.

In an aspect, said polypeptide comprises at least about 50%, 75%, 85%, 90%, 95%, 99%, or 100% identity to the sequence HMYFLLGH (SEQ ID NO: 5), GSLLVHSFQQLG (SEQ ID NO: 6), DPYDHEFR (SEQ ID NO: 7), AYYEEAYE (SEQ ID NO: 8), RYVDHEDW (SEQ ID NO: 9), EWELHAEE (SEQ ID NO: 10), SQSSMYPS (SEQ ID NO: 11), RYQLHHPR (SEQ ID NO: 12), WYKLHPTM (SEQ ID NO: 13), or a biologically active variant thereof.

In an aspect, the polypeptide comprises a conservative amino acid substitution.

In an aspect, the polypeptide comprises the sequence HMYFLLGH (SEQ ID NO: 5), GSLLVHSFQQLG (SEQ ID NO: 6), DPYDHEFR (SEQ ID NO: 7), AYYEEAYE (SEQ ID NO: 8), RYVDHEDW (SEQ ID NO: 9), EWEL-HAEE (SEQ ID NO: 10), SQSSMYPS (SEQ ID NO: 11), RYQLHHPR (SEQ ID NO: 12), WYKLHPTM (SEQ ID NO: 13), KLQLVLAPLHSLAS (SEQ ID NO: 14), or RSPGLAPARPRYA (SEQ ID NO: 15).

In an aspect, the polypeptide comprises from about 8 to about 300 amino acid residues, from about 8 to about 250 amino acid residues, from about 8 to about 200 amino acid residues, from about 8 to about 100 amino acid residues, from about 8 to about 50 amino acid residues, from about 8 to about 30 amino acid residues, from about 8 to about 20 amino acid residues, from about 8 to about 16 amino acid residues, from about 8 to about 12 amino acid residues, or from about 12 to about 16 amino acid residues.

In an aspect, the polypeptide consists of the sequence HMYFLLGH (SEQ ID NO: 5), GSLLVHSFQQLG (SEQ ID NO: 6), DPYDHEFR (SEQ ID NO: 7), AYYEEAYE (SEQ ID NO: 8), RYVDHEDW (SEQ ID NO: 9), EWEL-HAEE (SEQ ID NO: 10), SQSSMYPS (SEQ ID NO: 11), RYQLHHPR (SEQ ID NO: 12), WYKLHPTM (SEQ ID NO: 13), KLQLVLAPLHSLAS (SEQ ID NO: 14), or RSPGLAPARPRYA (SEQ ID NO: 15).

In an aspect, the polypeptide is HMYFLLGH (SEQ ID NO: 5) or GSLLVHSFQQLG (SEQ ID NO: 6).

In an aspect, the polypeptide binds to EGFL7. In an aspect, the polypeptide binds to EGFL7 with nanomolar affinity. In an aspect, the polypeptide binds specifically to EGFL7. In an aspect, the polypeptide binds to the dimerization domain of EGFL7. In an aspect, the polypeptide modulates EGFL7 receptor binding. In an aspect, the polypeptide modulates EGFL7 activity. In an aspect, the polypeptide modulates tubulogenesis. In an aspect, the polypeptide modulates cell migration. In an aspect, the polypeptide modulates cell adhesion. In an aspect, the polypeptide modulates angiogenesis.

In an aspect, the polypeptide comprises a detectable label. In an aspect, the label is detectable using nuclear medicine techniques. In an aspect, the label is gadolinium.

In an aspect, the polypeptide is coupled to a pharmaceutical agent for targeted delivery of the pharmaceutical agent to a site containing expressed EGFL7 within a subject. In an aspect, the pharmaceutical agent is an anti-VEGF antibody. In an aspect, the pharmaceutical agent is coupled to said polypeptide via a nanoparticle.

In accordance with another aspect, there is provided a polypeptide comprising at least 90% identity to the sequence HMYFLLGH (SEQ ID NO: 5), or a biologically active variant thereof.

In an aspect, the polypeptide comprises at least 95%, 99%, or 100% identity to the sequence HMYFLLGH (SEQ ID NO: 5), or a biologically active variant thereof.

In an aspect, the polypeptide comprises a conservative amino acid substitution.

In an aspect, the polypeptide comprises the sequence HMYFLLGH (SEQ ID NO: 5).

In an aspect, the polypeptide comprises from about 8 to about 300 amino acid residues, from about 8 to about 200 amino acid residues, from about 8 to about 100 amino acid residues, from about 8 to about 50 amino acid residues, from about 8 to about 30 amino acid residues, from about 8 to about 20 amino acid residues, or from about 8 to about 12 amino acid residues.

In an aspect, the polypeptide consists of the sequence HMYFLLGH (SEQ ID NO: 5).

In an aspect, the polypeptide binds to EGFL7. In an aspect, the polypeptide binds to EGFL7 with nanomolar affinity. In an aspect, the polypeptide binds specifically to EGFL7. In an aspect, the polypeptide binds to the dimerization domain of EGFL7. In an aspect, the polypeptide modulates EGFL7 receptor binding. In an aspect, the polypeptide modulates EGFL7 activity. In an aspect, the polypeptide modulates tubulogenesis. In an aspect, the polypeptide modulates cell migration. In an aspect, the polypeptide modulates cell adhesion. In an aspect, the polypeptide modulates angiogenesis.

In an aspect, the polypeptide comprises a detectable label. In an aspect, the label is detectable using nuclear medicine techniques. In an aspect, the label is gadolinium.

In an aspect, the polypeptide is coupled to a pharmaceutical agent for targeted delivery of the pharmaceutical agent to a site containing expressed EGFL7 within a subject. In an aspect, the pharmaceutical agent is an anti-VEGF antibody. In an aspect, the pharmaceutical agent is coupled to said polypeptide via a nanoparticle.

In accordance with another aspect, there is provided a polypeptide comprising at least 90% identity to the sequence GSLLVHSFQQLG (SEQ ID NO: 6), or a biologically active variant thereof, wherein said polypeptide comprises from about 12 to about 250 amino acid residues.

In an aspect, the polypeptide comprises at least 95%, 99%, or 100% identity to the sequence GSLLVHSFQQLG (SEQ ID NO: 6), or a biologically active variant thereof.

In an aspect, the polypeptide comprises a conservative amino acid substitution.

In an aspect, the polypeptide comprises the sequence GSLLVHSFQQLG (SEQ ID NO: 6).

In an aspect, the polypeptide comprises from about 12 to about 200 amino acid residues, from about 12 to about 100 amino acid residues, from about 12 to about 50 amino acid residues, from about 12 to about 30 amino acid residues, from about 12 to about 20 amino acid residues, or from about 12 to about 16 amino acid residues.

In an aspect, the polypeptide consists of the sequence GSLLVHSFQQLG (SEQ ID NO: 6).

In an aspect, the polypeptide binds to EGFL7. In an aspect, the polypeptide binds to EGFL7 with nanomolar affinity. In an aspect, the polypeptide binds specifically to EGFL7. In an aspect, the polypeptide binds to the dimerization domain of EGFL7. In an aspect, the polypeptide modulates EGFL7 receptor binding. In an aspect, the polypeptide modulates EGFL7 activity. In an aspect, the polypeptide modulates tubulogenesis. In an aspect, the polypeptide modulates cell migration. In an aspect, the polypeptide modulates cell adhesion. In an aspect, the polypeptide modulates angiogenesis.

In an aspect, the polypeptide comprises a detectable label. In an aspect, the label is detectable using nuclear medicine techniques. In an aspect, the label is gadolinium.

In an aspect, the polypeptide is coupled to a pharmaceutical agent for targeted delivery of the pharmaceutical agent to a site containing expressed EGFL7 within a subject. In an aspect, the pharmaceutical agent is an anti-VEGF antibody. In an aspect, the pharmaceutical agent is coupled to said polypeptide via a nanoparticle.

In accordance with another aspect, there is provided a polypeptide selected from the group consisting of DPYD-HEFR (SEQ ID NO: 7), AYYEEAYE (SEQ ID NO: 8), RYVDHEDW (SEQ ID NO: 9), EWELHAEE (SEQ ID NO: 10), SQSSMYPS (SEQ ID NO: 11), RYQLHHPR (SEQ ID NO: 12), WYKLHPTM (SEQ ID NO: 13), KLQLV-LAPLHSLAS (SEQ ID NO: 14), RSPGLAPARPRYA (SEQ ID NO: 15), and biologically active variants thereof.

In an aspect, there is provided a nucleic acid coding for the polypeptide, a vector comprising the nucleic acid, and a cell comprising the vector.

In another aspect, there is provided a composition or a medicament comprising the polypeptide, the nucleic acid, or the cell, together with a pharmaceutically acceptable carrier and/or an anti-angiogenic agent, such as an anti-VEGF antibody.

In another aspect, there is provided a method for treating pathological angiogenesis, said method comprising administering the polypeptide described herein to a subject in need thereof.

In another aspect, there is provided a use of the polypeptide described herein for treating pathological angiogenesis.

In an aspect, the pathological angiogenesis is a disease or condition selected from the group consisting of cancer, arthritis, cardiovascular disease, age-related macular degeneration, and diabetic retinopathy. In an aspect, the pathological angiogenesis is cancer.

In another aspect, there is provided a method of screening for pathological angiogenesis in a subject, the method comprising administering the polypeptide comprising the detectable label described herein to a subject and imaging the subject to detect said label, wherein detection of said label is suggestive of pathological angiogenesis in said subject.

In another aspect, there, is provided a use of the polypeptide comprising the detectable label described herein for screening for pathological angiogenesis in a subject, wherein detection of said label is suggestive of pathological angiogenesis in said subject.

In an aspect, detection of said label is diagnostic of pathological angiogenesis in said subject. In another aspect, the pathological angiogenesis is a disease or condition selected from the group consisting of cancer, arthritis, cardiovascular disease, age-related macular degeneration, and diabetic retinopathy. In an aspect, the pathological angiogenesis is cancer.

In another aspect, there is provided a method of predicting cancer prognosis, the method comprising administering the polypeptide described herein to a subject with cancer and determining the presence of the polypeptide in the subject, wherein the presence of the polypeptide in the subject is predictive of poor prognosis as compared to the absence of the polypeptide in the subject.

In another aspect, there is provided a use of the polypeptide described herein for predicting cancer prognosis in a subject, wherein the presence of the polypeptide in the subject is predictive of poor prognosis as compared to the absence of the polypeptide in the subject.

In another aspect, there is provided a method of targeted drug delivery in a patient suffering from pathological angiogenesis, the method comprising administering the polypeptide linked to the pharmaceutical agent described herein to a subject.

In another aspect, there is provided a use of the polypeptide linked to the pharmaceutical agent described herein for targeted drug delivery in a patient suffering from pathological angiogenesis.

In an aspect, the pathological angiogenesis is a disease or condition selected from the group consisting of cancer, arthritis, cardiovascular disease, age-related macular degeneration, and diabetic retinopathy. In an aspect, the pathological angiogenesis is cancer.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which:

FIG. 8 shows the amino acid sequences of EGFL7 derived from human (SEQ ID NO: 1), mouse (SEQ ID NO: 2), *xenopus* (SEQ ID NO: 3), and zebrafish (SEQ ID NO: 4).

FIG. 12 shows Phosphorylation of Axl and VEGFR 1 RTKs in HUVECs are decreased upon treatment with LCE71. (a) HUVECs were treated with either Flag (control) or LCE71 peptide (200 NM) for 4 hours. Immunoprecipitation was performed using the 4G10 anti-phospho antibody coupled onto Protein A/G agarose. Western blot analyses were performed using the anti-Axl, anti-VEGFR1 and anti-GAPDH antibody. (b) Bar graph showing the mean signal intensity of each band obtained from western blot shown in (a). Quantitation was performed using the Volocity software (version 6.1.2, PerkinElmer). Values obtained from cell lysates were normalized to GAPDH.

DETAILED DESCRIPTION OF THE INVENTION

Figure 1:
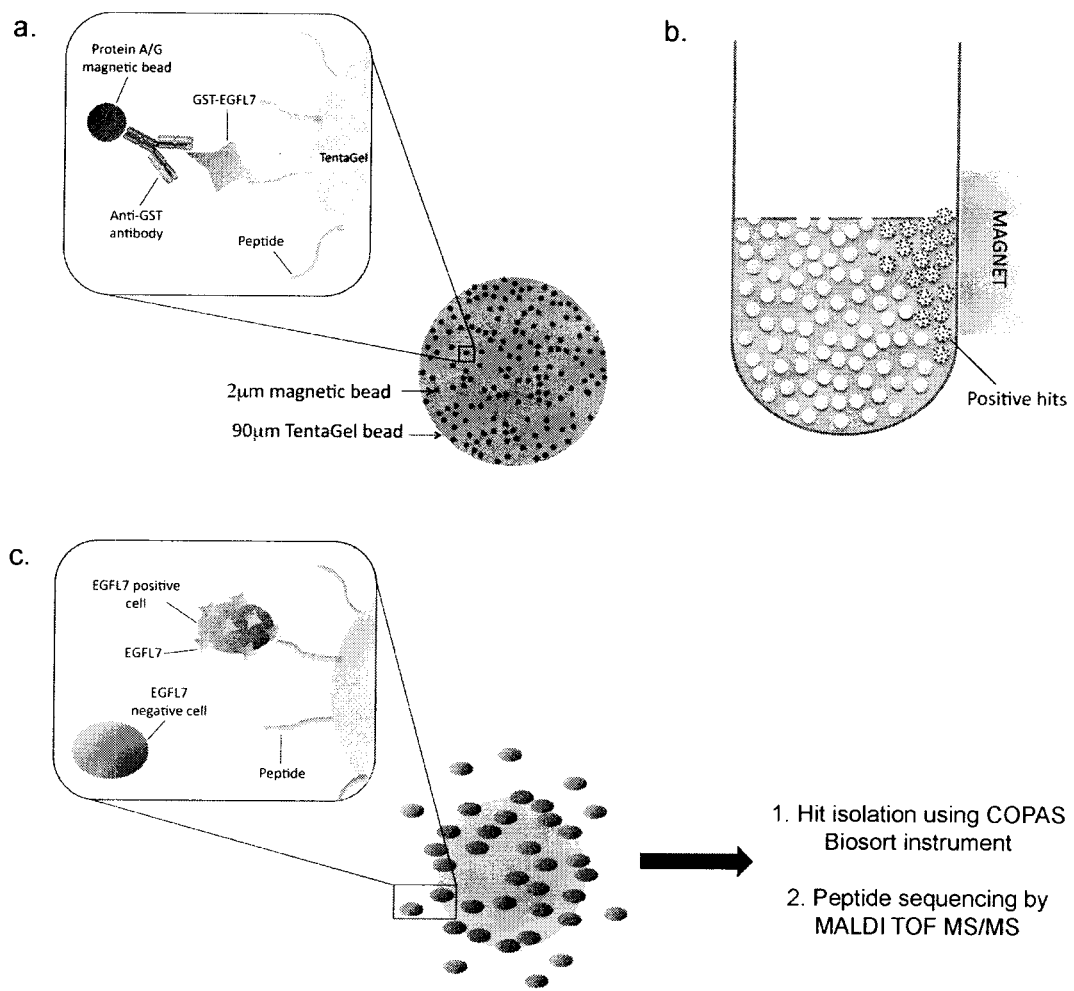
FIG. 1 shows a high-throughput strategy to screen an OBOC peptide library for high-affinity binding peptides against recombinant EGFL7 protein. (a) Schematic representation of the beads on a bead approach. Purified recombinant GST-EGFL7 protein was bound onto Protein A/G-coated magnetic beads via an anti-GST antibody, and mixed with a library of TentaGel beads displaying random 8-amino acid peptides. (b) TentaGel beads displaying high affinity peptides that strongly retained magnetic beads on their surfaces were isolated using a magnet. (c) Schematic representation of a secondary cell-based screen using EGFL7-positive HT1080-tdTomato cells and EGFL7-negative HT1080-GFP cells. Positive hit beads were isolated using the COPAS Biosort instrument (Union Biometrica), and peptides were sequenced on-bead using MALDI TOF MS/MS.

The present invention is directed to polypeptides that bind to and/or interact with EGFL7. EGFL7 is a protein that is up-regulated in the endothelium of tumours and other tissues that are undergoing active angiogenesis. EGFL7 expression correlates with poor prognosis in, for example, malignant glioma, hepatocellular carcinoma and non-small cell lung cancer and is a biomarker for clinically relevant neoplasms and metastases.

Herein, the identification and characterization of novel polypeptides that bind to and/or modulate EGFL7 activity to inhibit angiogenesis are described. The polypeptides were identified by screening a combinatorial peptide library using a novel 'beads on a bead' approach and were then tested for anti-angiogenic activity in vitro and in vivo. The polypeptides were also conjugated with a fluorescein dye and were found to effectively image EGFL7 expression through specific uptake and internalization in EGFL7-expressing cells.

Unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley. & Sons (New York, N.Y. 1994); Sambrook et al., Molecular Cloning. A Laboratory Manual, Cold Springs Harbor Press (Cold Springs Harbor, N.Y. 1989), each of which are incorporated herein by reference. For the purposes of the present invention, the following terms are defined below.

As used herein, the term "EGFL7" refers to the native polypeptide of EGFL7 and EGFL7 variant or mutant polypeptide sequences.

"Native sequence EGFL7" comprises a polypeptide having the same amino acid sequence as EGFL7 derived from nature, regardless of its mode of preparation or species. Thus, native sequence EGFL7 can have the amino acid sequence of naturally occurring human EGFL7, murine EGFL7, *Xenopus* EGFL7, zebrafish EGFL7 or EGFL7 from any other species. For example a typical full-length native sequence human EGFL7 amino acid sequence is set out in SEQ ID NO: 1. A native sequence mouse EGFL7 amino acid sequence is set out in SEQ ID NO: 2, a native sequence *Xenopus* EGFL7 is set out in SEQ ID NO: 3, and a native sequence zebrafish EGFL7 is set out in SEQ ID NO: 4. These sequences are shown in FIG. 8. Such native sequence EGFL7 can be isolated from nature or can be produced by recombinant and/or synthetic means. The term "native sequence EGFL7" specifically encompasses naturally occurring prepro, pro and mature forms and truncated forms of EGFL7, naturally occurring variant forms, and naturally occurring allelic variants.

"EGFL7 variants" are biologically active EGFL7 polypeptides having an amino acid sequence that differs from the sequence of a native sequence EGFL7 polypeptide, such as those set out in SEQ ID NOs: 1-4 for human, murine, Xenopus and zebrafish EGFL7 respectively, by virtue of an insertion, deletion, modification and/or substitution of one or more amino acid residues within the native sequence. EGFL7 variants generally have less than 100% sequence identity with a native sequence EGFL7, such as the human EGFL7 of SEQ ID NO: 1. Ordinarily, however, a biologically active EGFL7 variant will have an amino acid sequence with at least about 70% amino acid sequence identity with the amino acid sequence of a naturally occurring EGFL7 such as the human EGFL7 of SEQ ID NO: 1, typically at least about 75%, more typically at least about 80%, even more typically at least about 85%, even more typically at least about 90%, and even more typically of at least about 95% to at least about 99% amino acid sequence identity, in 1% increments. The EGFL7 variants include peptide fragments of at least 3 amino acids that retain a biological activity of the corresponding native sequence EGFL7 polypeptide. EGFL7 variants also include EGFL7 polypeptides wherein one or more amino acid residues are added at the N- or C-terminus of, or within, a native EGFL7 sequence. EGFL7 variants also include EGFL7 polypeptides where a number of amino acid residues are deleted and optionally substituted by one or more amino acid residues. EGFL7 variants also may be covalently modified, for example by substitution with a moiety other than a naturally occurring amino acid or by modifying an amino acid residue to produce a non-naturally occurring amino acid. EGFL7 variants may comprise a heparin binding domain.

"Percent amino acid sequence identity" is defined herein as the percentage of amino acid residues in the candidate sequence that are identical with the residues in the sequence of interest, such as the polypeptides of the invention, after aligning the sequences and introducing gaps, if necessary, to achieve the maximum percent sequence identity, and not considering any conservative substitutions as part of the sequence identity. None of N-terminal, C-terminal-, or internal extensions, deletions or insertions into the candidate sequence shall be construed as affecting sequence identity or homology. Methods and computer programs for the alignment are well known in the art, such as "BLAST".

"Active" or "activity" for the purposes herein refers to a biological and/or an immunological activity of native or naturally-occurring EGFL7, wherein "biological" activity refers to a biological function (either inhibitory or stimulatory) caused by a native or naturally-occurring EGFL7.

Thus, "biologically active" or "biological activity" when used in conjunction with "EGFL7" or "isolated EGFL7" means an EGFL7 polypeptide that exhibits or shares an effector function of native sequence EGFL7. One biological activity of EGFL7 is its ability to promote vascular formation. Other biological activities of EGFL7 include promotion of endothelial cell migration and adhesion. Typically, the EGFL7 biological activity is the ability to regulate tubulogenesis.

"Biologically active" or "biological activity" when used in conjunction with variant EGFL7 interacting polypeptides means that the variant EGFL7 interacting polypeptide exhibits or shares an effector function of the parent EGFL7 interacting polypeptide sequence. The biological activity of the variant EGFL7 interacting polypeptide sequence may be increased or decreased as compared with the parent EGFl7 interacting polypeptide.

The terms "inhibit" or "inhibitory" mean that a function or activity of EGFL7 is decreased, limited, blocked, or neutralized. These terms encompass a complete or partial inhibition in EGFL7 function or activity, including the binding of EGFL7 to its receptor.

An "EGFL7 receptor" is a molecule to which EGFL7 binds and which mediates the biological properties of EGFL7.

"Isolated" refers to a molecule that has been purified from its source or has been prepared by recombinant or synthetic methods and purified. Purified polypeptides are substantially free of other polypeptides or peptides.

"Substantially free" herein means less than about 5%, typically less than about 2%, more typically less than about 1%, even more typically less than about 0.5%, most typically less than about 0.1% contamination with other source proteins. "Essentially pure" protein means a composition comprising at least about 90% by weight of the protein, based on total weight of the composition, typically at least about 95% by weight, more typically at least about 90% by weight, even more typically at least about 95% by weight, and even more typically at least about 99% by weight of protein, based on total weight of the composition.

As used herein, "treatment" or "therapy" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of cellular degeneration or damage, such as the pathology of tumour cells in cancer treatment, or may render the cells more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat cancer. Effective amounts of the polypeptides described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the polypeptide, the responsiveness of the patient to the polypeptide, or a combination thereof. It will also be appreciated that the effective dosage of the polypeptide used for the treatment may increase or decrease over the course of a particular treatment regime. Changes in dosage may result and become apparent by standard diagnostic assays known in the art. The polypeptides of the present invention may, in aspects, be administered before, during or after treatment with conventional anti-cancer agents, radiotherapy, hormone therapy, biotherapy, and/or surgical tumour resection.

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

"Tumour", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumours), and Meigs' syndrome.

A "chemotherapeutic agent" is a chemical compound useful in the treatment of cancer. Examples of chemotherapeutic agents include alkylating agents such as thiotepa, CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins such as bullatacin and bullatacinone; camptothecins such as topotecan; bryostatin; callystatin; CC-1065 and its adozelesin, carzelesin and bizelesin synthetic analogues; cryptophycins such as cryptophycin 1 and cryptophycin 8; dolastatin; duocarmycins such as the synthetic analogues KW-2189 and CB1-TM1; eleutherobin; pancratistatin; sarcodictyins; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics, for example calicheamicin, especially calicheamicin gamma1I and calicheamicin omega1I, dynemicin, including dynemicin A, bisphosphonates, such as clodronate, esperamicins, neocarzinostatin chromophore and related chromoprotein enediyne antibiotic chromophores; aclacinomysins; actinomycin; authramycin; azaserine; bleomycins; cactinomycin; carabicin; carminomycin; carzinophilin; chromomycins; dactinomycin; daunorubicin; detorubicin; 6-diazo-5-oxo-L-norleucine; ADRIAMYCIN™ doxorubicin, including morpholino-doxorubicin, cyanomorpholino-doxorubicin, 2-pyrrolino-doxorubicin and deoxydoxorubicin; epirubicin; esorubicin; idarubicin; marcellomycin; mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilones; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethyihydrazide; procarbazine; PSK™ polysaccharide complex; razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethan; vindesine; dacarbazine; mannomustine; mitobronitol; mitolactol; pipobroman; gacytosine; arabinoside ("Ara-C"); taxoids, such as TAXOL™ paclitaxel, ABRAXANE™ Cremophor-free, albumin-engineered nanoparticle formulation of paclitaxel, TAXOTERE™ and doxetaxel; chloranbucil; GEMZAR™ gemcitabine; 6-thioguanine; mercaptopurine; methotrexate; platinum coordination complexes such as cisplatin, oxaliplatin and carboplatin; vinblastine; platinum; etoposide (VP-16); ifosfamide; vincristine; NAVELBINE™ vinorelbine; novantrone; teniposide; edatrexate; daunomycin; aminopterin; xeloda; ibandronate; irinotecans such as CPT-11; topoisomerase inhibitors such as RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumours such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestane, fadrozole, RIVISOR™ vorozole, FEMARA™ letrozole, and ARIMIDEX™ anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signalling pathways implicated in aberrant cell proliferation, such as, for example, PKC-alpha, Ralf and H-Ras; ribozymes such as a VEGF expression inhibitor (e.g., ANGIOZYME™ ribozyme) and a HER2 expression inhibitor; antibodies such as an anti-VEGF antibody (e.g., AVASTIN™ antibody); vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; and pharmaceutically acceptable salts, acids or derivatives of any of the above.

An "intraocular neovascular disease" is a disease characterized by ocular neovascularization. Examples of intraocular neovascular diseases include, but are not limited to, proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, Central Retinal Vein Occlusion (CRVO), corneal neovascularization, and retinal neovascularization.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmacologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, and dextrins; chelating agents such as EDTA; sugar alcohols such as mannitol and sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of a drug (such as a chemotherapeutic agent) to a subject, such as a mammal. The components of the liposome are commonly arranged in a bilayer formation, similar to the lipid arrangement of biological membranes.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Polypeptides

The present invention encompasses polypeptides that interact with EGFL7 and therefore modulate the function and/or activity of EGFL7. The EGFL7 interacting polypeptides typically bind to EGFL7 and act by modulating the binding of co-factors to EGFL7, by modulating the proper folding of the EGFL7 polypeptide, by modulating proper post-translational processing of EGFL7, by modulating EGFL7 binding to its receptor, or by modulating EGFL7 dimerization or multimerization. It is also possible that the EGFL7 interacting polypeptides are structural mimetics of EGFL7.

EGFL7 contains several domains, including a signalling sequence, a carboxy-terminal (matrilin-like) domain, a Notch binding domain, a dimerization domain and an amino-terminal domain. The EGFL7 interacting polypeptides typically bind to a specific domain of EGFL7, such as the carboxy-terminal domain or the dimerization domain. The EGFL7 interacting polypeptides may bind to the Notch domain and therefore exert their action through modulation of Notch binding to EGFL7. However, typically the EGFL7 interacting polypeptides bind outside of the Notch binding domain and do not affect Notch binding. In a specific aspect, the EGFL7 interacting polypeptides act independently of Notch binding.

Examples of EGFL7 interacting polypeptide sequences include HMYFLLGH (SEQ ID NO: 5), GSLLVHSFQQLG (SEQ ID NO: 6), DPYDHEFR (SEQ ID NO: 7), AYYEEAYE (SEQ ID NO: 8), RYVDHEDW (SEQ ID NO: 9), EWELHAEE (SEQ ID NO: 10), SQSSMYPS (SEQ ID NO: 11), RYQLHHPR (SEQ ID NO: 12), WYKLHPTM (SEQ ID NO: 13), KLQLVLAPLHSLAS (SEQ ID NO: 14), and RSPGLAPARPRYA (SEQ ID NO: 15) and biologically active variants thereof. These EGFL7 interacting polypeptides have been shown to bind to or interact with EGFL7 and inhibit angiogenesis. The EGFL7 interacting polypeptide sequence may consist of any one of sequences of SEQ ID NOs: 5-15 or biologically active variants thereof or it may comprise any one of the sequences of SEQ ID NOs: 5-15 or biologically active variants thereof. Combinations of these sequences and/or other EGFL7 interacting polypeptide sequences may also be employed and may act together synergistically or additively.

Sequences comprising the EGFL7 interacting polypeptides of the invention may comprise any number of amino acid residues, however, they typically comprise at least about 3 amino acid residues, from about 8 to about 300 amino acid residues, from about 8 to about 250, from about 8 to about 200 amino acid residues, from about 8 to about 100 amino acid residues, from about 8 to about 50 amino acid residues, from about 8 to about 30 amino acid residues, from about 8 to about 20 amino acid residues, from about 8 to about 16 amino acid residues, from about 8 to about 12 amino acid residues, or from about 12 to about 16 amino acid residues, with any single number increment within these ranges being specifically contemplated herein, such as, for example, 8, 9, 10, 11, 12, 13, 14, 15, or 16 amino acid residues.

Biologically active variants encompass any variant sequences of SEQ ID NOs: 5-13 that retain EGFL7 interacting activity. The EGFL7 interacting activity of the variant sequence may be the same as that of the parent sequence of SEQ ID NOs: 5-13, or it may be increased or reduced as compared to the parent sequence.

For example, acetylated sequences are contemplated, such as the sequence Ac-GSLLVHSFQQLG (SEQ ID NO: 6), wherein the "Ac" indicates acetylation of the polypeptide. For example, conservative amino acid substitutions within these sequences are contemplated. Examples of conservative amino acid substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, in H. Neurath and R. L. Hill, 1979, The Proteins, Academic Press, New York, which is incorporated by reference herein in its entirety. The most commonly occurring substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Thus, independently, one or both of the histidine residues in HMYFLLGH (SEQ ID NO: 5) could be substituted with arginine or lysine; the methionine residue could be substituted with glycine, alanine, serine, or threonine; the tyrosine residue could be substituted with phenylalanine or tryptophan; the phenylalanine residue could be substituted with tyrosine or tryptophan; one or both of the leucine residues could be substituted with isoleucine or valine; the glycine residue could be substituted with alanine, serine, threonine or methionine; or any combination thereof.

Similarly, independently, one or both of the glycine residues in GSLLVHSFQQLG (SEQ ID NO: 6) could be substituted with alanine, serine, threonine or methionine; one or both of the serine residues could be substituted with glycine, alanine, threonine or methionine; any one or more of the leucine residues could be substituted with isoleucine or valine; the valine residue could be substituted with leucine or isoleucine; the histidine residue could be substituted with arginine or lysine; the phenylalanine residue could be substituted with tyrosine or tryptophan; one or both of the glutamine residues could be substituted with asparagine; or any combination thereof.

Sequence variants of SEQ ID NOs: 7-13 could be similarly determined.

Alternatively, the amino acid changes within the EGFL7 interacting polypeptide sequences are of such a nature that the physico-chemical properties of the polypeptides are altered. For example, amino acid changes may improve the thermal stability of the polypeptide, alter the substrate specificity, change the pH optimum, and the like. For example, any one or more of the amino acids in the polypeptide sequences may be in the levo or dextro rotatory forms. Racemic mixtures may also be employed.

Amino acids that are required for biological activity in a parent polypeptide can be identified according to procedures known in the art, such as site-directed mutagenesis (Cunningham and Wells, 1989, Science 244: 1081-1085, incorporated herein by reference in its entirety). The active site of the biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; and Wlodaver et al., 1992, FEBS Lett. 309: 59-64, each of which is incorporated herein by reference in its entirety. The identities of amino acids that are required for biological activity can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625, each of which is incorporated by reference herein in its entirety. Other methods that can be used include error-prone PCR, phage display (e.g., Lowman et al., 1991, Biochemistry 30: 10832-10837; U.S. Pat. No. 5,223,409; and WO 92/06204, each of which is incorporated herein by reference in its entirety), and region-directed mutagenesis (Derbyshire et al., 1986, Gene 46: 145; and Ner et al., 1988, DNA 7: 127, each of which is incorporated by reference herein in its entirety).

Mutagenesis/shuffling methods can be combined with high-throughput, automated screening methods to detect activity of cloned, mutagenized polypeptides expressed by host cells (Ness et al., 1999, Nature Biotechnology 17: 893-896, incorporated by reference in its entirety). Mutagenized DNA molecules that encode active polypeptides can be recovered from the host cells and rapidly sequenced using standard methods in the art. These methods allow the rapid determination of the importance of individual amino acid residues in a polypeptide.

Also encompassed by variant EGFL7 interacting polypeptides are hybrid polypeptides, in which a portion of the EGFL7 interacting polypeptide is fused at the N-terminus or the C-terminus to another polypeptide or portion thereof.

The variant EGFL7 interacting polypeptide may be a fused polypeptide or cleavable fusion polypeptide in which another polypeptide is fused at the N-terminus or the C-terminus of the EGFL7 interacting polypeptide. A fused polypeptide is produced by fusing a polynucleotide encoding another polypeptide to a polynucleotide encoding the EGFL7 interacting polypeptide. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology, in which fusions are created post-translationally (see, for example, Cooper et al., 1993, EMBO J. 12: 2575-2583; and Dawson et al., 1994, Science 266: 776-779, each of which is incorporated herein by reference in its entirety).

A fusion polypeptide can further comprise a cleavage site between the fused polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48, each of which is incorporated by reference herein in its entirety.

Typically, biologically active variants of the EGFL7 interacting polypeptides, for example HMYFLLGH (SEQ ID NO: 5) or GSLLVHSFQQLG (SEQ ID NO: 6), have at least about 50% sequence identity to the EGFL7 interacting polypeptide sequences More typically, the sequence identity is at least about 60%, 70%, 75%, 80%, 85%, 90%, 91%, 92%, 93%, 94%, 95%, 96%, 97%, 98%, or 99% to the EGFL7 interacting polypeptide sequences.

The EGFL7 interacting polypeptides may also comprise a detectable label. "Detectable labels" are compounds and/or elements that can be detected due to their specific functional properties, and/or chemical characteristics, the use of which allows the EGFL7 polypeptide to which they are attached to be detected, and/or further quantified if desired.

Polypeptide diagnostics generally fall within two classes, those for use in in vitro diagnostics and/or those for use in vivo diagnostic protocols that are detected using various imaging techniques, such as nuclear imaging techniques. It will be understood that EGFL7 interacting polypeptides used for imaging may be modulatory peptides that modulate the activity of EGFL7 or they may not have any biological activity and may simply bind to EGFL7.

Many appropriate imaging agents are known in the art, as are methods for their attachment to polypeptides (see, for e.g., U.S. Pat. Nos. 5,021,236; 4,938,948; and 4,472,509, each of which is incorporated herein by reference in its entirety). The imaging moieties used can be, for example, paramagnetic ions; radioactive isotopes; fluorochromes; NMR-detectable substances; or X-ray imaging-detectable substances.

In the case of paramagnetic ions, examples include as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being typically used. Ions useful in other contexts, such as X-ray imaging, include but are not limited to lanthanum (III), gold (III), lead (II), and especially bismuth (III).

In the case of radioactive isotopes for therapeutic and/or diagnostic application, examples include $^{211}$astatine, $^{11}$carbon, $^{14}$carbon, $^{51}$chromium, $^{36}$chlorine, $^{57}$cobalt, $^{58}$cobalt, $^{64}$copper, $^{67}$copper, $^{152}$europium, $^{18}$fluorine, $^{67}$gallium, $^{68}$gallium, $^{3}$hydrogen, $^{123}$iodine, $^{125}$iodine, $^{111}$indium, $^{59}$iron, $^{32}$phosphorus, $^{186}$rhenium, $^{188}$rhenium, $^{75}$selenium, $^{35}$sulphur, $^{99m}$technicium and/or $^{90}$yttrium. $^{125}$Iodine is often used in certain embodiments, and $^{99m}$technicium and/or $^{111}$indium are also often used due to their low energy and suitability for long range detection. Radioactively labeled polypeptides may be produced according to well-known methods in the art. For instance, polypeptides can be iodinated by contact with sodium and/or potassium iodide and a chemical oxidizing agent such as sodium hypochlorite, or an enzymatic oxidizing agent, such as lactoperoxidase. Polypeptides may be labeled with $^{99m}$technecium by ligand exchange process, for example, by reducing pertechnate with stannous solution, chelating the reduced technecium onto a Sephadex column and applying the polypeptide to this column. Alternatively, direct labeling techniques may be used, e.g., by incubating pertechnate, a reducing agent such as $SNCl_2$, a buffer solution such as sodium-potassium phthalate solution, and the polypeptide. Intermediary functional groups that are often used to bind radioisotopes which exist as metallic ions to polypeptides are diethylenetriaminepentaacetic acid (DTPA), ethylene diaminetetracetic acid (EDTA), or 1,4,7,10-tetraazacyclododecane-1,4,7,10-tetraacetic acid (DOTA). Polypeptides may be labelled with fluorine-18 using prosthetic group methodology, whereby a small molecule is first radiolabeled and then is coupled to the peptide, for example, [$^{18}$fluorine]-fluorobenzoic acid is prepared and then coupled to an amino group of the peptide.

The fluorescent labels contemplated for use as detectable labels include, for example, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, fluorescein, fluorescein isothiocyanate (FITC), HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red. Typically, the fluorescent label is fluorescein.

Another class of polypeptide/detectable label conjugates contemplated for use in the present invention includes those that are intended primarily for use in vitro, where the polypeptide is linked to a secondary binding ligand and/or to an enzyme (an enzyme tag) that will generate a coloured product upon contact with a chromogenic substrate. Examples of suitable enzymes include urease, alkaline phosphatase, horseradish peroxidase, hydrogen peroxidase, glucose oxidase and combinations thereof. Typical secondary binding ligands are biotin and/or avidin and streptavidin compounds. The use of such labels is well known to those of skill in the art and is described, for example, in U.S. Pat. Nos. 3,817,837; 3,850,752; 3,939,350; 3,996,345; 4,277, 437; 4,275,149 and 4,366,241; each of which is incorporated herein by reference in its entirety.

Molecules containing azido groups may also be used to form covalent bonds to polypeptides through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; and Atherton et al., 1985, each of which is incorporated by reference herein in its entirety). The 2- and 8-azido nucleotides have also been used to map nucleotide binding domains of purified proteins (Khatoon et al., 1989; King et al., 1989; and Dholakia et al., 1989) and may be used as polypeptide binding agents.

Several methods are known in the art for the attachment or conjugation of a polypeptide to its detectable label. Some attachment methods involve the use of a metal chelate complex employing, for example, an organic chelating agent such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the polypeptide (see, for example, U.S. Pat. Nos. 4,472,509 and 4,938,948, each of which is incorporated herein by reference in its entirety). Polypeptides may also be reacted with an enzyme in the presence of a coupling agent such as glutaraldehyde or periodate. Conjugates with fluorescein markers may be prepared in the presence of these coupling agents or by reaction with an isothiocyanate. Detectable labels may also be bound to the polypeptide using linkers such as methyl-p-hydroxybenzimidate or N-succinimidyl-3-(4-hydroxyphenyl)propionate (see, for example, U.S. Pat. No. 4,938,948, incorporated by reference herein in its entirety).

Because EGFL7 is specifically expressed in tissues undergoing active angiogenesis, the EGFL7 interacting polypeptide may be coupled to a pharmaceutical agent, such as a chemotherapeutic agent, for targeted delivery of that pharmaceutical agent to a site containing expressed EGFL7. In this way, the pharmaceutical agent can be delivered only to areas of the body that are undergoing active angiogenesis, such as a tumour, for example. Any pharmaceutical agent or chemotherapeutic agent may be coupled to the EGFL7 interacting polypeptide. In an aspect, the chemotherapeutic agent is an anti-angiogenic agent such as an anti-VEGF antibody.

The EGFL7 interacting polypeptide may be coupled to the pharmaceutical agent via liposomes, nanocapsules, microparticles, microspheres, nanoparticles, lipid particles, vesicles, and the like, for targeting the pharmaceutical agent to a region of expressed EGFL7 within the body of a subject. Typically, the pharmaceutical agent may be formulated for delivery either encapsulated in a lipid particle, a liposome, a vesicle, a nanosphere, or a nanoparticle for example, with at least a portion of the EGFL7 interacting peptide being exposed for interacting with expressed EGFL7.

The formation and use of liposomes is generally known to those of skill in the art (see for example, Couvreur et al., FEBS Lett. 1977 Dec. 15; 84(2):323-6; Couvreur, Crit Rev Ther Drug Carrier Syst. 1988; 5(1):1-20; Lasic, Trends Biotechnol. 1998 July; 16(7):307-21; Gabizon & Papahadjopoulos, Proc Natl Acad Sci USA. 1988 September; 85(18): 6949-53; Allen and Chonn, FEBS Lett. 1987 Oct. 19; 223(1):42-6; U.S. Pat. No. 5,741,516, which are incorporated by reference herein in their entirety). Further, various methods of liposome and liposome like preparations as potential drug carriers have been reviewed (Takakura, Nippon Rinsho, 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each of which is incorporated herein by reference in its entirety).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the pharmaceutical agents. They are widely suitable as both water- and lipid-soluble substances can be entrapped, i.e. in the aqueous spaces and within the bilayer itself, respectively.

In addition to the teachings of Couvreur et al. FEBS Lett. 1977 Dec. 15; 84(2):323-6; and Couvreur et al., Crit Rev Ther Drug Carrier Syst. 1988; 5(1):1-20, the following information may be utilized in generating liposomal formulations. Phospholipids can form a variety of structures other than liposomes when dispersed in water, depending on the molar ratio of lipid to water. At low ratios the liposome is the typical structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most typical liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

The EGFL7 interacting polypeptides may be used to bind to the liposome surface and to direct the liposome and its drug contents to regions in the body that contain expressed EGFL7.

Alternatively, pharmaceutically-acceptable nanocapsule formulations may be used to entrap pharmaceutical agents in a stable and reproducible way (Henry-Michelland et al., J Pharm Pharmacology. 1987 December; 39(12):973-7; Quintanar-Guerrero et al., Drug Dev Ind Pharm. 1998 December; 24(12):1113-28; Douglas et al., Crit Rev Ther Drug Carrier Syst. 1987; 3(3):233-61, each of which is incorporated by reference herein in its entirety). To avoid side effects due to intracellular polymeric overloading, such ultrafine particles (sized around 0.1 µm) should be designed using polymers able to be degraded in vivo. For example, biodegradable polyalkyl-cyanoacrylate nanoparticles that meet these requirements are contemplated for use in the present invention. Such particles may be easily made, as described (Couvreur et al., 1980 supra and 1988, supra; zur Muhlen et al., Eur J Pharm Biopharm. 1998 March; 45(2):149-55; Zambaux et al. J Control Release. 1998 Jan. 2; 50(1-3):31-40; Pinto-Alphandry et al., 1995 J Drug Target. 1995; 3(2):167-9 and U.S. Pat. No. 5,145,684, each of which is incorporated herein by reference in its entirety).

The EGFL7 interacting polypeptides may be formulated into compositions, which may further comprise one or more pharmaceutically acceptable excipients, carriers, buffers, stabilizers, adjuvants, or mixtures thereof.

Therapeutic compositions of EGFL7 interacting polypeptides are prepared for storage by mixing the desired polypeptide having the appropriate degree of purity with optional pharmaceutically acceptable carriers, excipients, and/or stabilizers (Remington's Pharmaceutical Sciences, 16th edition, Osol, A. ed. (1980), incorporated herein by reference in its entirety), in the form of lyophilized formulations or aqueous solutions. Acceptable carriers, excipients, or stabilizers are nontoxic to recipients at the dosages and concentrations employed and are described above.

Additional examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms may be used. Such forms include, for example, microcapsules, nano-capsules, liposomes, plasters, inhalation forms, nose sprays, sublingual tablets, and sustained-release preparations.

EGFL7 interacting polypeptides will typically be formulated in such vehicles at a concentration of about 0.1 mg/ml to about 100 mg/ml.

Another formulation comprises incorporating EGFL7 interacting polypeptides into formed articles. Such articles can be used in modulating endothelial cell growth and angiogenesis. En addition, tumour invasion and metastasis may be modulated with these articles.

EGFL7 interacting polypeptides to be used for in vivo administration are generally sterile. This is readily accomplished, for example, by filtration through sterile filtration membranes, prior to or following lyophilization and reconstitution. EGFL7 interacting polypeptides ordinarily will be stored in lyophilized form or in solution if administered systemically. If in lyophilized form, EGFL7 interacting polypeptides are typically formulated in combination with other ingredients for reconstitution with an appropriate diluent at the time of use. An example of a liquid formulation of EGFL7 interacting polypeptides is a sterile, clear, colorless unpreserved solution filled in a single-dose vial for subcutaneous injection. Preserved pharmaceutical compositions suitable for repeated use may contain, for example, depending mainly on the indication and type of polypeptide: EGFL7 interacting polypeptides; a buffer capable of maintaining the pH in a range of maximum stability of the polypeptide in solution, typically about 4-8; a detergent/surfactant primarily to stabilize the polypeptide against agitation-induced aggregation; an isotonifier; a preservative selected from the group of phenol, benzyl alcohol and a benzethonium halide, e.g., chloride; and water.

If the detergent employed is non-ionic, it may, for example, comprise polysorbates (e.g., POLYSORBATE™ (TWEEN™) 20, 80, etc.) or poloxamers (e.g., POLOXAMER™ 188). The use of non-ionic surfactants permits the formulation to be exposed to shear surface stresses without causing denaturation of the polypeptide. Further, such surfactant-containing formulations may be employed in aerosol devices such as those used in a pulmonary dosing, and needleless jet injector guns (see, e.g., EP 257,956, incorporated herein by reference in its entirety).

An isotonifier may be present to ensure isotonicity of a liquid composition of EGFL7 interacting polypeptides, and includes polyhydric sugar alcohols, typically trihydric or higher sugar alcohols, such as glycerin, erythritol, arabitol, xylitol, sorbitol, and mannitol. These sugar alcohols can be used alone or in combination. Alternatively, sodium chloride or other appropriate inorganic salts may be used to render the solutions isotonic.

The buffer may, for example, be an acetate, citrate, succinate, or phosphate buffer depending on the pH desired. The pH of one type of liquid formulation of this invention is buffered in the range of about 4 to 8, typically about physiological pH.

The preservatives phenol, benzyl alcohol and benzethonium halides, e.g., chloride, are known antimicrobial agents that may be employed.

Therapeutic EGFL7 interacting polypeptide compositions described herein generally are placed into a container having a sterile access port, for example, an intravenous solution bag or vial having a stopper pierceable by a hypodermic injection needle. The formulations are typically administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956, incorporated herein by reference in its entirety).

An article of manufacture, such as a kit containing EGFL7 interacting polypeptides useful for the diagnosis or treatment of the disorders described herein, comprises at least a container and a label. Suitable containers include, for example, bottles, vials, syringes, and test tubes. The containers may be formed from a variety of materials such as glass or plastic. The container holds a composition that is effective for diagnosing or treating the condition and may have a sterile access port (for example, the container may be an intravenous solution bag or a vial having a stopper pierceable by a hypodermic injection needle). The active agent in the composition is an EGFL7 interacting polypeptide. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use. The article of manufacture may also comprise a second or third container with another active pharmaceutical agent as described herein.

EGFL7 interacting polypeptides can also be administered in the form of sustained-released preparations. Suitable examples of sustained-release preparations include semipermeable matrices of solid hydrophobic polymers containing the polypeptide, which matrices are in the form of shaped articles, e.g., films or microcapsules. Examples of sustained-release matrices include polyesters, hydrogels (e.g., poly(2-hydroxyethyl-methacrylate) as described by Langer et al., 1 Biomed. Mater. Res. 15:167-277 (1981) and Langer, Chem. Tech. 12:98-105 (1982) or poly(vinylalcohol)), polylactides (U.S. Pat. No. 3,773,919, EP 58,481), copolymers of L-glutamic acid and gamma ethyl-L-glutamate (Sidman et al., Biopolymers 22:547-556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988). Each of these references is incorporated herein by reference in its entirety.

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular disulfide bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release EGFL7 interacting polypeptide compositions also include liposomally entrapped EGFL7 interacting polypeptides. Liposomes containing the EGFL7 interacting polypeptides are prepared by methods known per se: DE 3,218,121; Epstein et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324, each of which is incorporated herein by reference. Ordinarily the liposomes are of the small (about 200-800 Angstroms) unilamellar type in which the lipid content is greater than about 30 mol. % cholesterol, the selected proportion being adjusted for the optimal therapy.

The therapeutically effective dose of the EGFL7 interacting polypeptides will, of course, vary depending on such factors as the pathological condition to be treated (including prevention), the method of administration, any co-therapy involved, the subject's age, weight, general medical condition, medical history, etc., and its determination is well within the skill of a practicing physician. Accordingly, it will be necessary for the clinician to titer the dosage and modify the route of administration as required to obtain the maximal therapeutic effect. The clinician will administer the EGFL7 interacting polypeptide until a dosage is reached that achieves the desired effect for treatment of the condition in question. For example, if the objective is the treatment of cancer, the amount would be, in one aspect, one that inhibits tumour growth.

With the above guidelines, the effective dose generally is within the range of from about 0.001 to about 1.0 mg/kg, more typically from about 0.01-1.0 mg/kg, and most typically from about 0.01-0.1 mg/kg.

For non-oral use, EGFL7 interacting polypeptides may be administered in the form of an injection at about 0.01 to 50 mg, typically about 0.05 to about 20 mg, most typically about 1 to about 20 mg, per kg body weight, 1 to 3 times daily by intravenous injection. For oral administration, an EGFL7 interacting polypeptide is typically administered at about 5 mg to about 1 g, typically about 10 to about 100 mg, per kg body weight, 1 to 3 times daily. It should be appreciated that endotoxin contamination should be kept minimally at a safe level, for example, less than about 0.5 ng/mg protein. Moreover, for human administration, the formulations generally meet sterility, pyrogenicity, general safety, and purity as required by the FDA Office and Biologics standards.

The route of EGFL7 polypeptide or antagonist or agonist administration is in accord with known methods, e.g., by injection or infusion by intravenous, intramuscular, intracerebral, intraperitoneal, intracerebrospinal, subcutaneous, intraocular, intraarticular, intrasynovial, intrathecal, oral, topical, or inhalation routes, or by sustained-release systems. EGFL7 interacting polypeptides also are suitably administered by intratumoural, peritumoural, intralesional, or perilesional routes, to exert local as well as systemic therapeutic effects. The intraperitoneal route is expected to be particularly useful, for example, in the treatment of ovarian tumours.

The effectiveness of an EGFL7 interacting polypeptide in preventing or treating the disorder in question may be improved by administering the polypeptide serially or in combination with another pharmacological agent that is effective for those purposes, either in the same composition or as separate compositions.

For example, EGFL7 interacting polypeptides used to treat angiogenesis-associated conditions such as cancer or ocular diseases may be combined with cytotoxic, chemotherapeutic, or anti-angiogenic agents as identified above and may act synergistically or additively with such other agents. In a tumour model, EGFL7 was found to remain in the tracks of regressed tumour vessels after the tumour was treated with an anti-VEGF antibody (see U.S. 2007/0031437, incorporated herein by reference in its entirety). Not wishing to be bound by a particular theory, it is possible that EGFL7 acts to support EC migration along the existing ECM tracks, and thus assists in tumour vessel regrowth subsequent to an anti-angiogenesis treatment. Therefore, it is desirable to use the EGFL7 interacting polypeptide in combination with an anti-angiogenic agent to enhance or sensitize the activity of the anti-angiogenic agent. In an aspect, the EGFL7 interacting polypeptide is used in combination with the anti-VEGF antibody bevacizumab to enhance its anti-tumour efficacy.

Lucentis™ is an Fab fragment of Avastin™ (bevacizumab) that is specifically indicated and approved for treatment of "wet" age-related macular degeneration. It is therefore also desirable to use the EGFL7 interacting polypeptide in combination with Lucentis™, or another anti-angiogenic agent, for the treatment of "wet" age-related macular degeneration.

The effective amounts of the therapeutic agents administered in combination with EGFL7 interacting polypeptides will be at the physician's or veterinarian's discretion. Dosage administration and adjustment is done to achieve maximal management of the conditions to be treated. The dose will additionally depend on such factors as the type of the therapeutic agent to be used and the specific patient being treated. Typically, the amount employed will be the same dose as that used, if the given therapeutic agent is administered without the EGFL7 interacting polypeptides.

Methods of Identifying EGFL7 Interacting Polypeptides

The present invention also encompasses methods of screening polypeptides to identify those that interact with EGFL7 and modulate and EGFL7 activity and/or function. In a specific aspect, a combinatorial peptide library is screened using a "beads on a bead" approach, as set out in FIG. 1 and described in Cho et al., which is incorporated herein by reference in its entirety. In this approach, a one bead one compound (OBOC) library is synthesized on 90 μm Tentagel, whereby each bead displays a unique octapeptide. Magnetic nanobeads are then coated with full-length recombinant EGFL7, are mixed with the peptide library, and the most highly interacting library bead "hits" are sorted using large format flow cytometry. An on-bead cell binding assay can then be used to validate the peptide hits using human endothelial cells. Validated hit peptides are then sequenced using an in-house MALDI-TOF/MS technique, and their binding affinity to EGFL7 is quantified using surface plasmon resonance (SPR) (Amadei et al. 2009, J. Mass Spectrometry, 45:241-51; U.S. Pat. Nos. 5,510,240; and 7,262,269, each of which is incorporated by reference herein in its entirety).

More generally, candidate EGFL7 interacting polypeptides are typically identified first in an assay that allows for the rapid identification of potential modulators of EGFL7 activity. An example of such an assay is a protein-protein binding assay wherein the ability of the candidate molecule to bind to an EGFL7 receptor is measured. In another example, the ability of the candidate molecule to interfere with EGFL7 binding to an EGFL7 receptor is measured. Methods of identifying compounds that bind to and/or interact with EGFL7 are set out in U.S. 2007/0031437, which is incorporated herein by reference in its entirety.

Such methods are set out briefly below as they relate to identification of polypeptides.

In an aspect, EGFL7 interacting polypeptides are identified by their ability to modulate (i.e., inhibit or enhance) one or more of the biological activities of EGFL7. Thus a candidate polypeptide is contacted with EGFL7. The biological activity of EGFL7 is then assessed. In one aspect, the ability of EGFL7 to stimulate endothelial cell proliferation is determined. In another aspect, the ability of the EGFL7 to promote endothelial cell survival is determined. In other aspects, the ability of the EGFL7 to promote endothelial cell migration, adhesion, or tube formation is determined. A polypeptide is identified as an EGFL7 interacting polypeptide where the biological activity of EGFL7 is modulated in the presence of the polypeptide.

Additionally, any method suitable for detecting protein-protein interactions may be employed for identifying polypeptides that interact with EGFL7. Among the traditional methods that may be employed are co-immunoprecipitation, crosslinking and co-purification through gradients or chromatographic columns to identify polypeptides that interact with EGFL7. For such assays, the EGFL7 component can be a full-length protein, a soluble derivative thereof, a peptide corresponding to a domain of interest, or a fusion protein containing some region of EGFL7.

Methods may be employed that result in the simultaneous identification of genes that encode proteins capable of interacting with EGFL7. These methods include, for example, probing expression libraries, in a manner similar to the well-known technique of antibody probing of Δgt11 libraries, using labeled EGFL7 or a variant thereof.

A method that detects protein interactions in vivo, the two-hybrid system, is described in detail for illustration only and not by way of limitation. One version of this system has been-described (Chien et al., Proc. Natl. Acad. Sci. USA 88:9578-9582 (1991), which is incorporated herein by reference in its entirety) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a nucleotide sequence encoding EGFL7, or a polypeptide, peptide, or fusion protein therefrom, and the other plasmid consists of nucleotides encoding the transcription activator protein's activation domain fused to a cDNA encoding an unknown polypeptide which has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, EGFL7 can be used as the bait gene product. Total genomic or cDNA sequences are fused to the DNA encoding an activation domain. This library and a plasmid encoding a hybrid of a bait EGFL7 gene product fused to the DNA-binding domain are co-transformed into a yeast reporter strain, and the resulting transformants are screened for those that express the reporter gene. For example, and not by way of limitation, a bait EGFL7 gene sequence, e.g., the gene's open reading frame, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which polypeptides that interact with the bait EGFL7 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait EGFL7 gene-GALA fusion plasmid into a yeast strain that contains a lacZ gene driven by a promoter which contains a GALA activation sequence. A cDNA encoded polypeptide, fused to GAL4 transcriptional activation domain, that interacts with the bait EGFL7 gene product will reconstitute an active GAL4 protein and thereby drive expression of the reporter gene. Colonies that drive expression of the reporter gene can be detected by methods routine in the art. The cDNA can then be purified from these strains, and used to produce and isolate the bait EGFL7 gene-interacting polypeptide using techniques routinely practiced in the art.

Computer modeling and searching technologies permit identification of polypeptides, or the improvement of already identified polypeptides, that can modulate EGFL7 function or activity. Having identified such a polypeptide, the active sites or regions of interaction with EGFL7 are identified. Such active sites might typically be ligand binding sites. The active site can be identified using methods known in the art including, for example, from the amino acid sequences of peptides, from the nucleotide sequences of nucleic acids, or from study of complexes of the relevant polypeptide with EGFL7. In the latter case, chemical or X-ray crystallographic methods can be used to find the active site by finding where on EGFL7 the complexed polypeptide is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed polypeptide, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as polypeptides, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site (or binding site), either experimentally, by modeling, or by a combination, candidate interacting polypeptides can be identified by searching databases containing compounds along with information on their molecular structure. Such a search seeks polypeptides having structures that match the determined active site structure and that interact with the groups defining the active site. Such a search can be manual, but is typically computer assisted. The polypeptides found from this search are potential modulators of EGFL7 activity.

Alternatively, these methods can be used to identify improved interacting polypeptides from an already known interacting compound or ligand. The composition of the known polypeptide can be modified and the structural effects of modification can be determined using the experimental and computer modeling methods described above applied to the new composition. The altered structure is then compared to the active site structure of the complex to determine if an improved fit or interaction results. In this manner systematic variations in composition, such as by varying side groups, can be quickly evaluated to obtain modified interacting polypeptides of improved specificity or activity.

Further experimental and computer modeling methods useful to identify interacting polypeptides based upon identification of the active sites (or binding sites) of EGFL7 will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behaviour of molecules with each other.

Although described above with reference to design and generation of polypeptides that could alter binding, one could also screen libraries of known polypeptides and/or libraries of novel polypeptides for EGFL7 interacting polypeptides.

Systems may be designed to identify polypeptides capable of interacting with (e.g., binding to) or capable of interfering with the binding of EGFL7 to a cognate receptor, binding partner or substrate. The polypeptides identified can be useful, for example, in modulating the activity of wild type and/or mutant EGFL7 gene products; can be useful in elaborating the biological function of EGFL7; can be utilized in screens for identifying compounds that disrupt normal EGFL7 interactions; or may themselves disrupt or activate such interactions.

The principle of the assays used to identify polypeptides that bind to EGFL7, or EGFL7 cognate receptors or substrates, involves preparing a reaction mixture of EGFL7 and the test polypeptide under conditions and for a time sufficient to allow the two components to interact and bind, thus forming a complex which can be removed and/or detected in the reaction mixture. The EGFL7 species used can vary depending upon the goal of the screening assay. For example, where antagonists of the natural receptor are desired, the full-length EGFL7, or a soluble truncated EGFL7, a peptide, or fusion protein containing one or more EGFL7 domains fused to a protein or polypeptide that affords advantages in the assay system (e.g., labeling, isolation of the resulting complex, etc.) can be utilized. Where compounds that directly interact with EGFL7 are sought, peptides corresponding to the EGFL7 and fusion proteins containing EGFL7 can be used, for example.

The screening assays can be conducted in a variety of ways. For example, one method to conduct such an assay would involve anchoring the EGFL7, polypeptide, peptide, or fusion protein therefrom, or the test polypeptide onto a solid phase and detecting EGFL7/test polypeptide complexes anchored on the solid phase at the end of the reaction. In one aspect of such a method, the EGFL7 may be anchored onto a solid surface, and the test polypeptide, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, typically a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized component on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for an EGFL7 protein, polypeptide, peptide or fusion protein or the test compound to anchor any complexes formed in solution, and a labeled antibody specific for the other component of the possible complex to detect anchored complexes.

Macromolecules that interact with EGFL7 are referred to, for purposes of this discussion, as "binding partners". These binding partners are likely to be involved in EGFL7 mediated biological pathways. Therefore, it is desirable to identify polypeptides that interfere with or disrupt the interaction of such binding partners which may be useful in regulating or augmenting EGFL7 activity in the body and/or controlling disorders associated with this activity (or a deficiency thereof).

The basic principle of the assay systems used to identify polypeptides that interfere with the interaction between EGFL7 and a binding partner or partners involves preparing a reaction mixture containing EGFL7, or some variant thereof, and the binding partner under conditions and for a time sufficient to allow the two to interact and bind, thus forming a complex. In order to test a polypeptide for inhibitory activity, the reaction mixture is prepared in the presence and absence of the test polypeptide. The test polypeptide may be initially included in the reaction mixture, or may be added at a time subsequent to the addition of the EGFL7 and its binding partner. Control reaction mixtures are incubated without the test polypeptide or with a control polypeptide. The formation of any complexes between the EGFL7 and the binding partner is then detected. The formation of a complex in the control reaction, but not in the reaction mixture containing the test polypeptide, indicates that the compound interferes with the interaction of the EGFL7 and its binding partner. Additionally, complex formation within reaction mixtures containing the test polypeptide and normal EGFL7 protein may also be compared to complex formation within reaction mixtures containing the test polypeptide and a mutant EGFL7. This comparison may be important in those cases wherein it is desirable to identify polypeptide that specifically disrupt interactions of mutant, or mutated, EGFL7 but not the normal proteins.

The assay for polypeptides that interfere with the interaction between EGFL7 and binding partners can be conducted in a heterogeneous or homogeneous format. Heterogeneous assays involve anchoring either the EGFL7, or the binding partner, onto a solid phase and detecting complexes anchored on the solid phase at the end of the reaction. In homogeneous assays, the entire reaction is carried out in a liquid phase. In either approach, the order of addition of reactants can be varied to obtain different information about the polypeptides being tested. For example, test polypeptides that interfere with the interaction by competition can be identified by conducting the reaction in the presence of the test polypeptide; i.e., by adding the test polypeptide to the reaction mixture prior to, or simultaneously with, EGFL7 and interactive binding partner. Alternatively, test polypeptides that disrupt preformed complexes, e.g. polypeptides with higher binding constants that displace one of the components from the complex, can be tested by adding the test polypeptide to the reaction mixture after complexes have been formed.

In a particular embodiment, an EGFL7 fusion protein can be prepared for immobilization. For example, EGFL7, or a peptide fragment thereof, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art. This antibody can be labeled with the radioactive isotope $^{125}$I, for example, by methods routinely practiced in the art. In a heterogeneous assay, the fusion protein can be anchored to glutathione-agarose beads. The interactive binding partner can then be added in the presence or absence of the test polypeptide in a manner that allows interaction and binding to occur. At the end of the reaction period, unbound material can be washed away, and the labeled monoclonal antibody can be added to the system and allowed to bind to the complexed components. The interaction between EGFL7 and the interactive binding partner can be detected by measuring the amount of radioactivity that remains associated with the glutathione-agarose beads. A successful inhibition of the interaction by the test polypeptide will result in a decrease in measured radioactivity.

Alternatively, the GST fusion protein and the interactive binding partner can be mixed together in liquid in the absence of the solid glutathione-agarose beads. The test polypeptide can be added either during or after the species are allowed to interact. This mixture can then be added to the glutathione-agarose beads and unbound material is washed away. Again the extent of inhibition of the interaction between EGFL7 and the binding partner can be detected by adding the labeled antibody and measuring the radioactivity associated with the beads.

EGFL7 interacting polypeptides that modulate binding of EGFL7 to its receptor may be detected by combining EGFL7 and a candidate polypeptide with membrane-bound EGFL7 receptors or recombinant receptors under appropriate conditions for a competitive inhibition assay. EGFL7 can be labeled, such as by radioactivity, such that the number of EGFL7 molecules bound to the receptor can be used to determine the effectiveness of the candidate polypeptide. In another assay for interacting EGFL7 polypeptides, mammalian cells or a membrane preparation expressing the EGFL7 receptor would be incubated with labeled EGFL7 in the presence of the candidate polypeptide. The ability of the polypeptide to enhance or block this interaction could then be measured.

Methods of Testing Candidate EGFL7 Interacting Polypeptides

Various assays can be used to test EGFL7 polypeptides for EGFL7 interacting activity. Such assays include those provided in the Examples below and those set out in U.S. 2007/0031437, which is incorporated herein by reference in its entirety.

For cancer, a variety of well-known animal models can be used to test the efficacy of candidate EGFL7 interacting polypeptides, such as small-molecule antagonists. The in vivo nature of such models makes them particularly predictive of responses in human patients. Animal models of tumours and cancers (e.g., breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumour cells into syngeneic mice using standard techniques, e.g., subcutaneous injection, tail vein injection, spleen implantation, intraperitoneal implantation, implantation under the renal capsule, or orthopin implantation, e.g., colon cancer cells implanted in colonic tissue. See, e.g., PCT publication No. WO 97/33551, published Sep. 18, 1997, which is incorporated herein by reference in its entirety. Probably the most often used animal species in oncological studies are immunodeficient mice and, in particular, nude mice. The observation that the nude mouse with thymic hypo/aplasia could successfully act as a host for human tumour xenografts has led to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII, and SJL. In addition, a wide variety of other animals with inherited immunological defects other than the nude mouse have been bred and used as recipients of tumour xenografts. For further details see, e.g., The Nude Mouse in Oncology Research, E. Boven and B. Winograd, eds. (CRC Press, Inc., 1991), which is incorporated herein by reference in its entirety.

The cells introduced into such animals can be derived from known tumour/cancer cell lines, such as, for example, the B 104-1-1 cell line (stable NIH-3T3 cell line transfected with the neu protooncogene); ras-transfected NIH-3T3 cells; Caco-2 cells (ATCC HTB-37); or a moderately well-differentiated grade II human colon adenocarcinoma cell line, HT-29 (ATCC HTB-38); or from primary tumours and cancers. Samples of tumour or cancer cells can be obtained from patients undergoing surgery, using standard conditions involving freezing and storing in liquid nitrogen. Karma et al., Br. J. Cancer 48:689-696 (1983), which is incorporated herein by reference in its entirety.

Tumour cells can be introduced into animals, such as nude mice or EGFL7 knockout mice, by a variety of procedures.

The subcutaneous (s.c.) space in mice is very suitable for tumour implantation. Tumours can be transplanted s.c. as solid blocks, as needle biopsies by use of a trochar, or as cell suspensions. For solid-block or trochar implantation, tumour tissue fragments of suitable size are introduced into the s.c. space. Cell suspensions are freshly prepared from primary tumours or stable tumour cell lines, and injected subcutaneously. Tumour cells can also be injected as subdermal implants. In this location, the inoculum is deposited between the lower part of the dermal connective tissue and the s.c. tissue.

Animal models of breast cancer can be generated, for example, by implanting rat neuroblastoma cells (from which the neu oncogene was initially isolated), or neu-transformed NIH-3T3 cells into nude mice, essentially as described by Drebin et al. Proc. Nat. Acad. Sci. USA 83:9129-9133 (1986), which is incorporated by reference herein in its entirety.

Similarly, animal models of colon cancer can be generated by passaging colon cancer cells in animals, e.g., nude mice, leading to the appearance of tumours in these animals. An orthotopic transplant model of human colon cancer in nude mice has been described, for example, by Wang et al., Cancer Research 54:4726-4728 (1994) and Too et al., Cancer Research 55:681-684 (1995), each of which is incorporated by reference herein in its entirety. This model is based on the so-called "METAMOUSE™" sold by AntiCancer, Inc., (San Diego, Calif.).

Tumours that arise in animals can be removed and cultured in vitro. Cells from the in vitro cultures can then be passaged to animals. Such tumours can serve as targets for further testing or polypeptide screening. For example, Meth A, CMS4, CMS5, CMS21, and WEHI-164 are chemically induced fibrosarcomas of BALB/c female mice (DeLeo et al., J. Exp. Med. 146:720 (1977), which is incorporated herein by reference in its entirety), which provide a highly controllable model system for studying the anti-tumour activities of various agents. Palladino et al., J. Immunol. 138:4023-4032 (1987), incorporated herein by reference in its entirety. Briefly, tumour cells are propagated in vitro in cell culture. Prior to injection into the animals, the cell lines are washed and suspended in buffer, at a cell density of about $10 \times 10^6$ to $10 \times 10^7$ cells/ml. The animals are then infected subcutaneously with 10 to 100 µl of the cell suspension, allowing one to three weeks for a tumour to appear.

In addition, the Lewis lung carcinoma of mice, which is one of the most thoroughly studied experimental tumours, can be used as an investigational tumour model. Efficacy in this tumour model has been correlated with beneficial effects in the treatment of human patients diagnosed with small-cell carcinoma of the lung (SCCL). This tumour can be introduced in normal mice upon injection of tumour fragments from an affected mouse or of cells maintained in culture. Zupi et al., Br. J. Cancer 41: suppl. 4, 30 (1980), incorporated herein by reference in its entirety. Evidence indicates that tumours can be started from injection of even a single cell and that a very high proportion of infected tumour cells survive. For further information about this tumour model see, Zacharski, Haemostasis 16:300-320 (1986), which is incorporated by reference herein in its entirety.

The efficacy of candidate EGFL7 interacting polypeptides can be tested also in the treatment of spontaneous animal tumours. An exemplary suitable target for such studies is the feline oral squamous cell carcinoma (SCC). Feline oral SCC is a highly invasive, malignant tumour that is the most common oral malignancy of cats, accounting for over 60% of the oral tumours reported in this species. It rarely metastasizes to distant sites, although this low incidence of metastasis may merely be a reflection of the short survival times for cats with this tumour. These tumours are usually not amenable to surgery, primarily because of the anatomy of the feline oral cavity. At present, there is no effective treatment for this tumour. Prior to entry into the study, each cat undergoes complete clinical examination and biopsy, and is scanned by computed tomography (CT). Cats diagnosed with sublingual oral squamous cell tumours may be excluded from the study as the tongue can become paralyzed as a result of such tumour. Thus, even if the treatment is effective against the tumour, the affected animal may not be able to feed itself. Each cat is treated repeatedly, over a longer period of time. Photographs of the tumours will be taken daily during the treatment period, and at each subsequent recheck. After treatment, each cat undergoes another CT scan. CT scans and thoracic radiograms are evaluated every 8 weeks thereafter. The data are evaluated for differences in survival, response, and toxicity as compared to control groups. Positive response may require evidence of tumour regression, typically with improvement of quality of life and/or increased life span.

In addition, other spontaneous animal tumours, such as fibrosarcoma, adenocarcinoma, lymphoma, chondroma, or leiomyosarcoma of dogs, cats, and baboons can also be tested. Of these, mammary adenocarcinoma in dogs and cats is a typical model as its appearance and behaviour are very similar to those in humans. However, the use of this model is limited by the rare occurrence of this type of tumour in animals.

One way of evaluating the efficacy of a test polypeptide in an animal model with an implanted tumour is to measure the size of the tumour before and after treatment. Traditionally, the size of implanted tumours has been measured with a slide calliper in two or three dimensions. The measure limited to two dimensions does not always accurately reflect the size of the tumour; therefore, it is usually converted into the corresponding volume by using a mathematical formula. However, the measurement of tumour size can be very inaccurate. The therapeutic effects of a polypeptide candidate can often be better described in terms of treatment-induced growth delay and specific growth delay. Another important variable in the description of tumour growth is the tumour volume doubling time. Computer programs for the calculation and description of tumour growth are also available, such as the program reported by Rygaard and Spang-Thomsen, Proc. 6th Int. Workshop on Immune-Deficient Animals, Wu and Sheng eds. (Basel, 1989), p. 301, which is incorporated by reference herein in its entirety.

Further, recombinant (transgenic) animal models can be engineered by introducing the coding portion of the EGFL7 gene into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (U.S. Pat. No. 4,873,191); retrovirus-mediated gene transfer into germ lines (e.g., Van der Putten et al., Proc. Natl. Acad. Sci. USA 82:6148-615 (1985)); gene targeting in embryonic stem cells (Thompson et al., Cell 56:313-321 (1989)); electroporation of embryos (Lo, Mol. Cell. Biol. 3:1803-1814 (1983)); and sperm-mediated gene transfer. Lavitrano et al., Cell 57:717-73 (1989). For a review, see for example, U.S. Pat. No. 4,736,866. Each of these references is incorporated herein by reference in its entirety.

Transgenic animals also include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., Proc. Natl. Acad. Sci. USA 89:6232-636 (1992). The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. Such animals can then be used to test the candidate EGFL7 interacting polypeptides.

Other in vitro and in vivo tests known in the art for measuring angiogenesis are also suitable herein for testing the efficacy of candidate EGFL7 interacting polypeptides. In one examples, endothelial cells, for example, human umbilical vein endothelial cells (HUVEC) or human microvascular endothelial cells (HMVEC), which can be prepared or obtained commercially, are mixed at a concentration of $2\times10^5$ cells/ml with fibrinogen (5 mg/ml in phosphate buffered saline (PBS) in a 1:1 (v/v) ratio. Thrombin is added (5 units/ml final concentration) and the mixture is immediately transferred to a 24-well plate (0.5 ml per well). A fibrin gel is allowed to form and then VEGF and bFGF are added to the wells (each at 5 ng/ml final concentration) along with the candidate polypeptide. The cells are incubated at 37° C. in 5% $CO_2$ for 4 days at which time the cells in each well are counted and classified as either rounded, elongated with no branches, elongated with one branch, or elongated with 2 or more branches. Results are often expressed as the average of 5 different wells for each concentration of polypeptide. Typically, in the presence of an angiogenic inhibitor, such as an EGFL7 interacting polypeptide, cells remain either rounded or form undifferentiated tubes (e.g. 0 or 1 branch).

This assay is recognized in the art to be predictive of anti-angiogenic efficacy in vivo (Min et al., 1996, which is incorporated by reference herein in its entirety).

In an alternate assay, endothelial cell tube formation is observed when endothelial cells are cultured on MATRIGEL™ (Schnaper et al., 1995, which is incorporated herein by reference in its entirety). Endothelial cells ($1\times10^4$ cells/well) are transferred onto MATRIGEL™-coated 24-well plates, and tube formation is quantitated after 48 hours. Candidate EGFL7 interacting polypeptides are tested by adding them either at the same time as the endothelial cells or at various time points thereafter.

This assay models angiogenesis by presenting to the endothelial cells a particular type of basement membrane, namely the layer of matrix which migrating and differentiating endothelial cells might be expected to first encounter. In addition to bound growth factors, the matrix components found in Matrigel™ (and in basement membranes in situ) or proteolytic products thereof may also be stimulatory for endothelial cell tube formation, which makes this model complementary to the fibrin gel angiogenesis model previously described (Blood and Zetter, 1990; Odedra and Weiss, 1991, each of which is incorporated herein by reference in its entirety). Candidate EGFL7 interacting polypeptides that inhibit endothelial cell tube formation in both assays suggests that such polypeptides will also have anti-angiogenic activity in vivo.

Additionally, widely accepted functional assays of angiogenesis and, hence, anti-angiogenic agents are the corneal micropocket assay of neovascularization and the chick chorioallantoic membrane assay (CAM) assay. U.S. Pat. No. 5,712,291 is specifically incorporated herein by reference to show that the corneal micropocket and CAM assays are sufficiently predictive to identify agents for use in the treatment of an extremely wide range of angiogenic diseases.

U.S. Pat. No. 5,001,116 is also specifically incorporated herein by reference for purposes of describing the CAM assay. In summary, fertilized chick embryos are removed from their shell on day 3 or 4, and a methylcellulose disc containing the test compound is implanted on the chorioallantoic membrane. The embryos are examined approximately 48 hours later and, if a clear avascular zone appears around the methylcellulose disc, the diameter of that zone is measured. As disclosed in U.S. Pat. No. 5,712,291, specifically incorporated herein by reference for this purpose, in the context of the present invention, the appearance of any avascular zone is sufficient to evidence an anti-angiogenic polypeptide. The larger the zone, the more effective the polypeptide.

The corneal micropocket assay of neovascularization may be practiced using rat or rabbit corneas. This in vivo model is widely accepted as being predictive of clinical usefulness, as evidenced by U.S. Pat. Nos. 5,712,291 and 5,871,723, each specifically incorporated herein by reference for evidence purposes.

In the present invention, the corneal micropocket assay can be used to identify an EGFL7 interacting polypeptide. This is evidenced by a significant reduction in angiogenesis, as represented by a consistently observed and, typically, marked reduction in the number of blood vessels within the cornea. Such responses are typically defined as those corneas showing only an occasional sprout and/or hairpin loop that displayed no evidence of sustained growth when contacted with the candidate polypeptide.

Methods of Treatment and Diagnosis Using EGFL7 Interacting Polypeptides

EGFL7 interacting polypeptides that have activity in the in vivo and/or in vitro assays described herein are likely to have therapeutic uses in a variety of disorders associated with pathological angiogenesis, including systemic disorders that affect vessels. Their therapeutic utility could include diseases of the arteries, capillaries, veins, and/or lymphatic vessels.

EGFL7 interacting polypeptides may also be employed to inhibit erythropoiesis or granulopoiesis, to inhibit wound healing or tissue regeneration and associated therapies concerned with excess re-growth of tissue, such as connective tissue, skin, bone, cartilage, muscle, lung, or kidney, to inhibit angiogenesis, to inhibit migration of endothelial cells, and to inhibit the growth of vascular smooth muscle and endothelial cell production. For example, the EGFL7 interacting polypeptides could be used to limit the production of excess connective tissue during wound healing or pulmonary fibrosis if EGFL7 promotes such production, thus, such polypeptides could find use in the treatment of acute myocardial infarction and heart failure.

Specific types of diseases are described below, where EGFL7 interacting polypeptides may find use as targeting moieties for site-specific pharmacological agent delivery or for treatment or prevention of the disorders. Atherosclerosis is a disease characterized by accumulation of plaques of intimal thickening in arteries, due to accumulation of lipids, proliferation of smooth muscle cells, and formation of fibrous tissue within the arterial wall. The disease can affect large, medium, and small arteries in any organ. Changes in endothelial and vascular smooth muscle cell function are known to play an important role in modulating the accumulation and regression of these plaques.

Hypertension is characterized by raised vascular pressure in the systemic arterial, pulmonary arterial, or portal venous systems. Elevated pressure may result from or result in impaired endothelial function and/or vascular disease.

Inflammatory vasculitides include giant cell arteritis, Takayasu's arteritis, polyarteritis nodosa (including the microangiopathic form), Kawasaki's disease, microscopic polyangiitis, Wegener's granulomatosis, and a variety of infectious-related vascular disorders (including Henoch-Schonlein prupura). Altered endothelial cell function has been shown to be important in these diseases.

Reynaud's disease and Reynaud's phenomenon are characterized by intermittent abnormal impairment of the circulation through the extremities on exposure to cold. Altered endothelial cell function has been shown to be important in this disease.

Aneurysms are saccular or fusiform dilatations of the arterial or venous tree that are associated with altered endothelial cell and/or vascular smooth muscle cells.

Arterial restenosis (restenosis of the arterial wall) may occur following angioplasty as a result of alteration in the function and proliferation of endothelial and vascular smooth muscle cells.

Thrombophlebitis and lymphangitis are inflammatory disorders of veins and lymphatic vessels, respectively, that may result from, and/or in, altered endothelial cell function. Similarly, lymphedema is a condition involving impaired lymphatic vessels resulting from endothelial cell function.

The family of benign and malignant vascular tumours are characterized by abnormal proliferation and growth of cellular elements of the vascular system. For example, lymphangiomas are benign tumours of the lymphatic system that are congenital, often cystic, malformations of the lymphatic vessels that usually occur in newborns. Cystic tumours tend to grow into the adjacent tissue and usually occur in the cervical and axillary region. They can also occur in the soft tissue of the extremities. The main symptoms are dilated, sometimes reticular, structured lymphatic vessels and lymphocysts surrounded by connective tissue. Lymphangiomas are assumed to be caused by improperly connected embryonic lymphatic vessels or their deficiency, resulting in impaired local lymph drainage.

Another use for EGFL7 interacting polypeptides is in the prevention or inhibition of tumour angiogenesis, which involves vascularization of a tumour to enable it to grow and/or metastasize. Thus, more broadly, the EGFL7 interacting polypeptides may find use in the treatment and/or prevention of cancer.

The EGFL7 interacting polypeptides can also be useful in treating intraocular neovascular diseases.

Rheumatoid arthritis is a further indication for EGFL7 interacting polypeptides. Blood vessel growth and targeting of inflammatory cells through the vasculature is an important component in the pathogenesis of rheumatoid and sero-negative forms of arthritis.

Other therapeutic regimens may be combined with the administration of the EGFL7 interacting polypeptides. For example, if the polypeptides are to treat cancer, the patient to be treated with such polypeptides may also receive radiation therapy. Alternatively, or in addition, a chemotherapeutic agent may be administered to the patient. Preparation and dosing schedules for such chemotherapeutic agents may be used according to the manufacturers' instructions or as determined empirically by the skilled practitioner. Preparation and dosing schedules for such chemotherapy are also described in Chemotherapy Service, Ed., M. C. Perry (Williams & Wilkins: Baltimore, Md., 1992), incorporated herein by reference. The chemotherapeutic agent may precede, or follow administration of the polypeptide, or may be given simultaneously therewith.

If the polypeptides are used for treating cancer, it may be desirable to also administer antibodies against EGFL7, such as those described in U.S. 2007/0031437 (incorporated by reference herein) or other antibodies against other tumour-associated antigens, such as antibodies that bind to one or more of the ErbB2, EGFR, ErbB3, ErbB4, or VEGF receptor(s). Also, the antibody is suitably administered serially or in combination with radiological treatments, whether involving irradiation or administration of radioactive substances. Alternatively, or in addition, two or more antibodies binding the same or two or more different antigens disclosed herein may be co-administered to the patient. Sometimes, it may be beneficial also to administer one or more cytokines to the patient. In an aspect, the polypeptides herein are co-administered with a growth-inhibitory agent. For example, the growth-inhibitory agent may be administered first, followed by an interacting polypeptide of the present invention. However, simultaneous administration or administration of the polypeptide first is also contemplated. Suitable dosages for the growth-inhibitory agent are those presently used and may be lowered due to the combined action (synergy) of the growth-inhibitory agent and the polypeptide herein.

In one aspect, vascularization of tumours is attacked in combination therapy. The EGFL7 interacting polypeptide and an antibody (e.g., anti-VEGF) are administered to tumour-bearing patients at therapeutically effective doses as determined, for example, by observing necrosis of the tumour or its metastatic foci, if any. Additional anti-tumour agents can be further administered, such as alpha-, beta-, or gamma-interferon, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumours, such as anti-protein C antibody, anti-protein S antibody, or C4b binding protein (see, WO 91/01753, incorporated herein by reference), or heat or radiation.

In other aspects, an FGF or PDGF antagonist, such as an anti-FGF or an anti-PDGF neutralizing antibody, is administered to the patient in conjunction with the EGFL7 interacting polypeptide. Treatment with the polypeptide may be suspended during periods of wound healing or desirable neovascularization.

In another aspect, EGFL7 can be used as a target for screening, diagnosis, and/or predicting prognosis of disease. For example, EGFL7 is a protein that is up-regulated in the endothelium of tumours and other tissues that are undergoing active angiogenesis. EGFL7 expression correlates with poor prognosis in several cancer types, including for example, malignant glioma, hepatocellular carcinoma and non-small cell lung cancer and is a biomarker for clinically relevant neoplasms and metastases. Specifically, EGFL7 interacting polypeptides are administered to a subject as set out above or are applied to a tumour sample ex vivo, such as a biopsy sample, in a diagnostically or prognostically effective amount. Such amounts may be sufficient to treat the cancer, or they may simply be sufficient to detect the presence of bound EGFL7 interacting polypeptides to EGFL7. The EGFL7 interacting polypeptides are generally labelled as set out above so that they can be imaged and their distribution within the body or sample can be determined. The presence of bound EGFL7 polypeptides can be a screening indicator that a subject should undergo further testing to obtain a diagnosis or the presence of bound EGFL7 can be diagnostic in and of itself. Additionally, if a patient has already been diagnosed with cancer, the presence of bound EGFL7 polypeptides can serve as a poor prognostic indicator, as compared to if there was an absence of bound EGFL7 polypeptides. The binding of EGFL7 polypeptides can be qualitative or quantitative and can therefore, in aspects, be used to provide more specific information about the disease state, grade, and prognosis of an individual subject. EGFL7 polypeptides can also be used in combination with other diagnostic or prognostic molecules, such as growth receptors over expressed in certain tumours, to provide more specific information about the tumour in question.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Examples

Example 1—Identification of Candidate EGFL7 Interacting Polypeptides

Methods:
Cloning and Expression of Recombinant EGFL7

EGFL7 cDNA was amplified by PCR (sense primer: 5'-CACCATGAGGGGCTCTCAGGAGGTG-3' (SEQ ID NO: 31) and anti-sense primer: 5'-CTACGAGTCTTTCTT-GCAGGAGCAG-3' (SEQ ID NO: 32)) and cloned into the pENTR/TEV/D-TOPO vector (Invitrogen) according to the manual's instruction. The TEV-EGFL7 region was cloned into pDEST20 plasmid (Invitrogen) by recombination and the recombinant bacmid DNA was isolated according to the Invitrogen manual's instruction.

Purification of Recombinant GST-EGFL7

Recombinant baculovirus was generated from *Spodoptera frugiperda*, Sf21 cells that were transfected with 1 mg of bacmid DNA using CellFECTIN tranfection reagent (Invitrogen). Plaque titration of the virus was performed according to the standard protocol described in the Invitrogen manual. Sf21 cells were seeded into a T175 cell culture flask with approximately 80% confluency. Upon cell attachment, the medium was removed and the cells were infected with the recombinant baculovirus at a multiplicity of infection (MOI) of 20 for 72 h at 27° C. The cell lysate was harvested in 0.1% NP40, and passed through 1 mL of glutathione-agarose resin. The column was then washed with 25 mL of buffer (150 mM NaCl, 20 mM Tris-HCl, pH 7.9), and eluted with buffer supplemented with 20 mM reduced glutathione. Elutions were collected in 1 mL fractions and stored at 4° C. All eluted fractions were analyzed using SDS-PAGE and visualized by silver staining.

Generation of EGFL7-Magnetic Beads

All fractions containing EGFL7 recombinant protein were pooled together. 30 μg of anti-GST antibody was mixed into the protein solution, and incubated with 370 mg of Magna-Bind Protein A/G magnetic beads (Thermo Scientific) for 15 minutes at 4° C. After several washing with wash buffer, the proteins were released from the magnetic beads by boiling in SDS loading buffer, and analyzed by western blot using anti-EGFL7 polyclonal antibody (R&D Systems).

Screening a OBOC Library

The OBOC peptide library beads were washed extensively using 70% ethanol, distilled water and binding buffer (50 mM $Na_2HPO_4$, 150 mM NaCl, 2 mM $CaCl_2$, 0.5M L-Arginine, pH 7.4) before screening. The magnetic beads were mixed with the library beads in a glass vial, and incubated at 37° C. for 1 hour, A strong magnet was placed at the side of the vial, and the library was screened as described in Cho et al. Positive hits were pooled and washed extensively with ethanol and water. A secondary cell-based screen was performed using EGFL7-positive HT1080 fibrosarcoma cells expressing tdTomato, and EGFL7-negative MDA435 breast cancer cells expressing GFP as described in Cho et al. Hit beads were collected and peptides were sequenced on-bead using MALDI TOF MS/MS as described in Cho et al.

Figure 2:
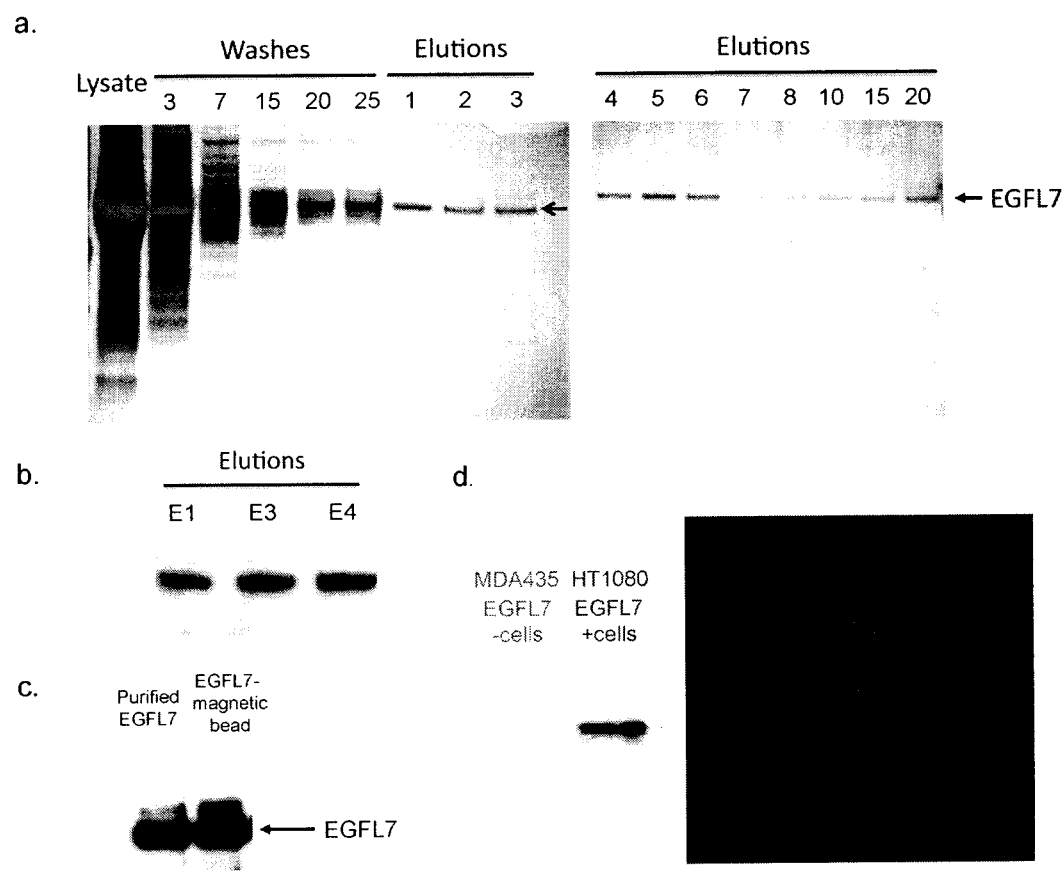
FIG. 2 shows the purification and identification of high-affinity binding peptides against recombinant EGFL7 protein. (a) Silver-stained gel showing the purification of recombinant GST-EGFL7 protein (left). (b) The eluted fractions were subjected to western blot analysis using a polyclonal anti-EGFL7 antibody. (c) Western blot analysis confirming the conjugation of purified EGFL7 protein onto the magnetic beads. (d) A secondary cell-based screening approach to identify peptides with high affinity for EGFL7 displayed on cell surface. Western blot analysis confirming the expression of EGFL7 in MDA435-GFP and HT1080-tdT-EGFL7v5 cells using a polyclonal anti-EGFL7 antibody (right). Fluorescence microscopic image of an example hit bead that strongly associated with red HT1080-tdT cells (+EGFL7), but have very little interaction with green MDA435-GFP cells (− EGFL7).

Results:

Recombinant EGFL7 protein was purified (FIGS. 2A and 2B) and conjugated onto magnetic beads. Western blot analysis was performed to show successful conjugation of purified EGFL7 onto magnetic beads using a polyclonal anti-EGFL7 antibody (FIG. 2C). EGFL7-conjugated magnetic beads were then mixed with a OBOC combinatorial peptide library, and positive hits were isolated using a strong neodynium magnet. A secondary cell-binding assay using EGFL7-positive red cells (TH1080-tdT-EGFL7v5) and EGFL7-negative green cells (MDA435-GFP) was used to identify peptides with high affinity for EGFL7 displayed on cell surface (FIG. 2D). Beads were examined under an inverted fluorescence microscope, and hit beads that strongly associated with red cells, but had little or no interaction with green cells were isolated manually.

The sequences HMYFLLGH (SEQ ID NO: 5), DPYD-HEFR (SEQ ID NO: 7), AYYEEAYE (SEQ ID NO: 8), RYVDHEDW (SEQ ID NO: 9), EWELHAEE (SEQ ID NO: 10), SQSSMYPS (SEQ ID NO: 11), RYQLHHPR (SEQ ID NO: 12), and WYKLHPTM (SEQ ID NO: 13) were identified as having high affinity for EGFL7 using the OBOC peptide library screening method.

Other exemplary EGFL7 interacting polypeptides are shown in Table 1. Column 1 in Table 1, labelled "LCE#," indicates the compound reference number. Column 2 in Table 1, labelled "Sequence," indicates the amino acid sequence of the peptide. Column 3 in Table 1, labelled "Purity," indicates the experimentally determined chemical purity using UV absorption at 220 nm frm reverse-phase HPLC analysis. Column 4 in Table 1, labelled "MS Calc," indicates the theoretical mass to charge ratio that is expected for the peptide when using electro-spray (positive ion mode) mass spectrometry. Column 5 in Table 1, labelled "MS Expt," indicates the experimentally determined mass to charge ratio that was found for the peptide when using electro-spray (positive ion mode) mass spectrometry.

TABLE 1

EGFL7 interacting polypeptides.

| LCE# | Sequence | Purity | MS calc | MS expt |
|---|---|---|---|---|
| 74 | Ac-KLQLVLAPLHSLAS-NH2 | >98% | $[M + 2H]^{2+} = 767.0$ | 768.2 |
| 83 | H-CKLQLVLAPLHSLAS-NH2 | >90% | $[M + 2H]^{2+} = 797.0$ | 796.8 |
| 136 | H-HMYFLLGH-NH2 | >99% | $[M + 2H]^{2+} = 1016.5$ | 1016.61 |
| 137 | H-HMYFLLGH(Ahx)(LysDOTA)-NH2 | >95% | $[M + 2H]^{2+} = 822.9$ | 824.7 |
| 171 | H-hMYFLLGH-NH2 | >95% | $[M + 2H]^{2+} = 508.8$ | 508.9 |
| 172 | H-hMYFLLGh(Ahx)(LysFITC)-NH2 | >95% | $[M + 2H]^{2+} = 824.4$ | 824.3 |
| 177 | H-HMYFLLGH(Ahx)(LysN3)-NH2 | >99% | $[M + H]^{+} = 1283.7$ | 1284.1 |
| 185 | H-hMYFLLGH-NH2 | >99% | $[M + H]^{+} = 1016.5$ | 1016.6 |
| 231 | H-H(DabN3)YFLLGH-NH2 | >99% | $[M + H]^{+} = 1012.2$ | 1011.8 |
| 232 | H-h(DabN3)YFLLGH-NH2 | >99% | $[M + H]^{+} = 1012.2$ | 1011.8 |
| 233 | H-H(DabN3)YFLLGh-NH2 | >99% | $[M + H]^{+} = 1012.2$ | 1011.7 |
| 234 | H-h(DabN3)YFLLGh-NH2 | >99% | $[M + H]^{+} = 1012.2$ | 1011.7 |
| 235 | H-H(Nle)YFLLGH-NH2 | >99% | $[M + H]^{+} = 999.2$ | 998.8 |
| 236 | H-h(Nle)YFLLGH-NH2 | >99% | $[M + H]^{+} = 999.2$ | 998.7 |
| 237 | H-H(Nle)YFLLGh-NH2 | >98% | $[M + H]^{+} = 999.2$ | 998.8 |
| 238 | H-h(Nle)YFLLGh-NH2 | >99% | $[M + H]^{+} = 999.2$ | 998.8 |

Note:
Lower case letter indicates D-amino acid

Example 2—Identification of Candidate EGFL7 Interacting Polypeptides Derived from EGFL7

Three highly conserved sequences from EGFL7 were chosen that are not present in EGFL8. The sequences identified were GSLLVHSFQQLG (SEQ ID NO: 6), KLQLVLAPLHSLAS (SEQ ID NO: 14), and RSPGLAPARPRYA (SEQ ID NO: 15).

Example 3—Validation of Identified EGFL7 Interacting Polypeptides

Methods:
Binding Studies

Peptides were immobilized onto gold spots using standard protocols from the GWC manual. Peptides were then exposed to 500 µL of purified EGFL7 protein. The % change in reflectivity (% R) for each of the spots containing the peptides was collected using V++ Precision Digital Imaging Systems, version 5.0 software and the dissociation constants ($K_D$) were calculated using the 'association then dissociation' equation in GraphPad Prism, version 5.0.

In Vitro Angiogenesis

A 96-well plate was coated with 50 mL per well of Matrigel. After the Matrigel has solidified, approximately 2000 HUVECs were seeded onto the polymerized matrix. VEGF (10 ng/ml) and bFGF (10 ng/ml) were added into each well as angiogenic stimuli. Either HMYFLLGH (SEQ ID NO: 5) or FLAG peptide (control) was introduced at a concentration of 200 mM into the appropriate wells before incubation at 37° C. in 5% $CO_2$. After 4-6 hours, the cells were imaged under an inverted microscope and the degree of tube formation was quantified by counting the number of branch points per field of view from each well.

In Vivo Avian Chorioallantoic Membrane (CAM) Angiogenesis Assay

An avian embryo chorioallantoic membrane (CAM) onplant assay was used to measure de novo angiogenesis. Collagen-enmeshed grids (<1 mm) were inoculated with HT1080 fibrosarcoma cells in the presence or absence of HMYFLLGH (SEQ ID NO: 5) (200 µM final concentration). HT1080 cells were cultured on fiber-mesh to stimulate the recruitment of blood vessels from the CAM onto the mesh. Collagen mesh onplants were placed on the CAM of day 9 shell-less embryos for 3 days before they were imaged using the Zeiss Lumar fluorescent stereomicroscope. The level of angiogenesis was quantified by counting the percentage of grids in each mesh that contains visible blood vessels.

Figure 3:
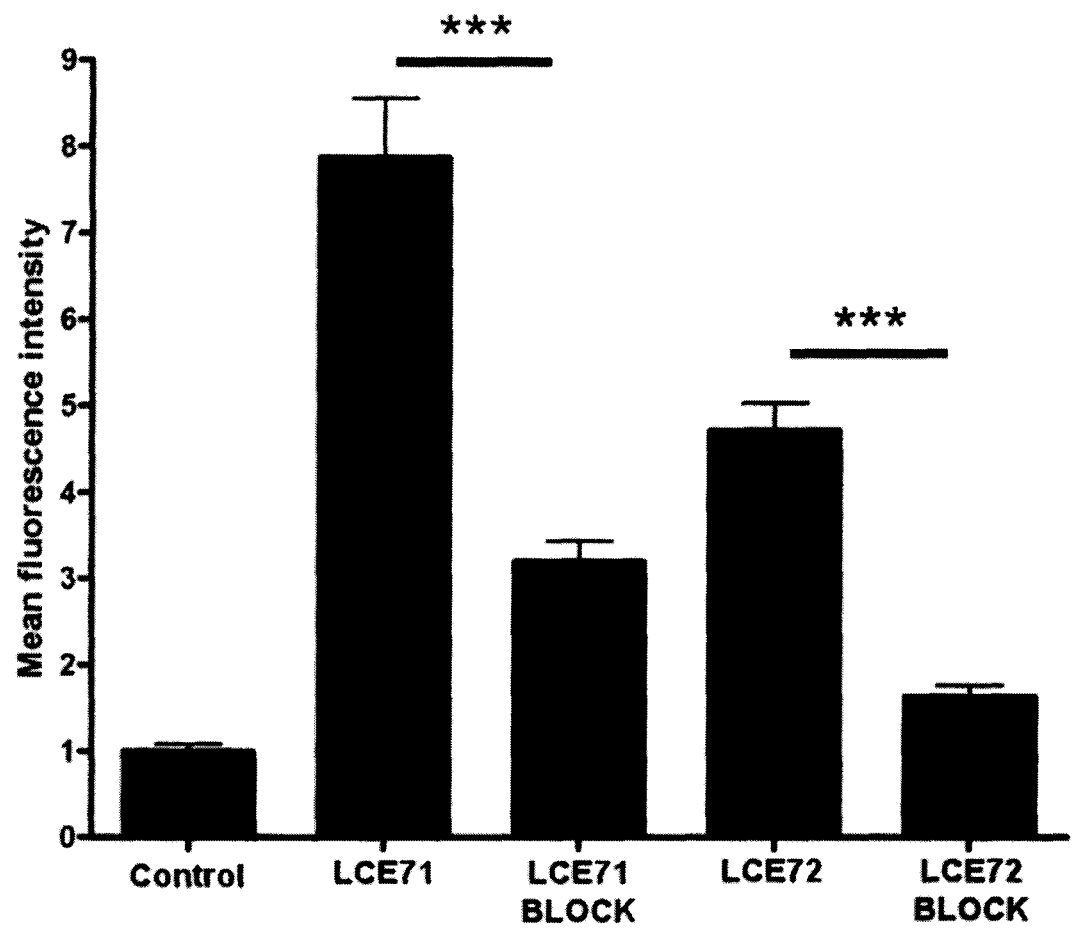
FIG. 3 shows that the sequences GSLLVHSFQQLG (LCE71/LCE77, SEQ ID NO: 6) and HMYFLLGH (LCE72/LCE78, SEQ ID NO: 5) bind to human endothelial cells expressing EGFL7 and are blocked by excess unlabelled peptide (p>0.001).

Results:

Using the binding study described above, binding affinities of 14.7 nM and 13.2 nM were calculated for GSLLVHSFQQLG (SEQ ID NO: 6) and HMYFLLGH (SEQ ID NO: 5), respectively (FIG. 3).

Figure 4:
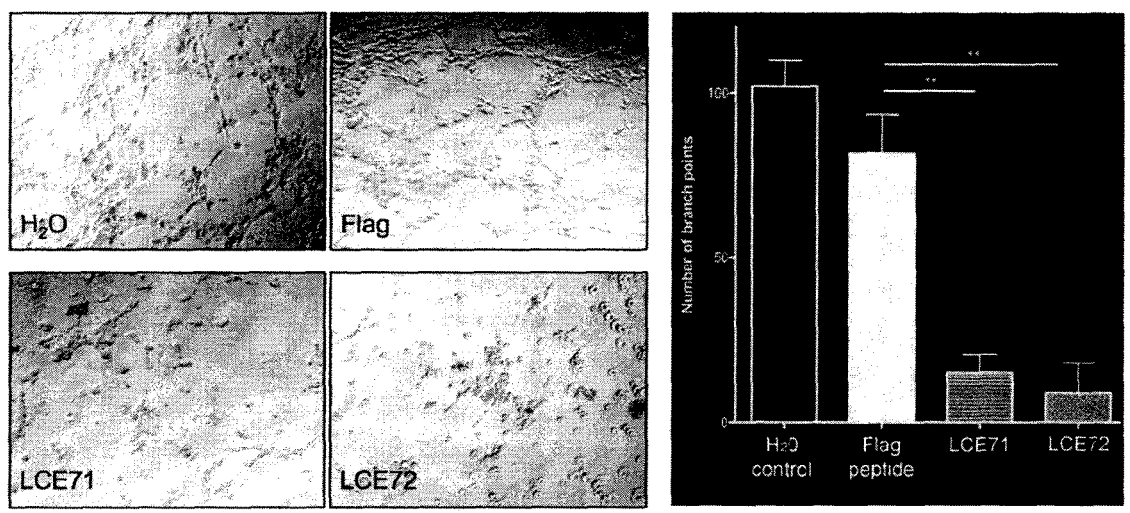
FIG. 4 shows an in vitro angiogenesis assay demonstrating that GSLLVHSFQQLG (SEQ ID NO: 6) and HMYFLLGH (SEQ ID NO: 5) inhibited human umbilical vein endothelial cell (HUVECs) sprouting and tube formation on Matrigel in the presence of VEGF and FGF compared to controls (FLAG peptide and H20). The level of sprouting was quantified by counting the number of branch points formed by the HUVECs.

The in vitro angiogenesis assay demonstrated that HMYFLLGH (SEQ ID NO: 5) inhibited human umbilical vein endothelial cell (HUVEC) sprouting and tube formation on Matrigel in the presence of VEGF and FGF as compared to controls (FLAG peptide and water) (FIG. 4). The level of sprouting was quantified by counting the number of branch points formed by the HUVEC cells (FIG. 4).

Figure 5:
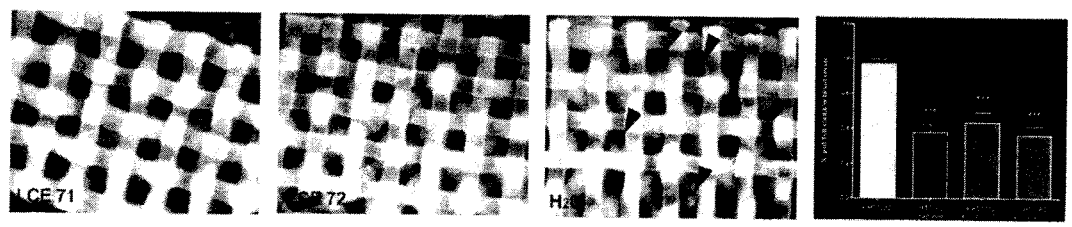
FIG. 5 shows an in vivo angiogenesis assay demonstrating that GSLLVHSFQQLG (SEQ ID NO: 6) and HMYFLLGH (SEQ ID NO: 5) significantly inhibited angiogenesis using the chicken chorioallantoic membrane (CAM) model. HT1080 cells were cultured in the fiber-mesh to stimulate the recruitment of blood vessels from the CAM onto the mesh. The level of angiogenesis was quantified by counting the percentage of grids within the mesh that contains visible blood vessels (indicated by arrows).

The in vivo angiogenesis assay demonstrated that HMYFLLGH (SEQ ID NO: 5) significantly inhibited angiogenesis using the chicken chorioallantoic membrane (CAM) model. HT1080 cells were cultured on the fiber-mesh to stimulate the recruitment of blood vessels from the CAM onto the mesh (FIG. 4). The level of angiogenesis was quantified by counting the percentage of grids within the mesh that contains visible blood vessels (indicated by red arrows) (FIG. 5).

Figure 6:
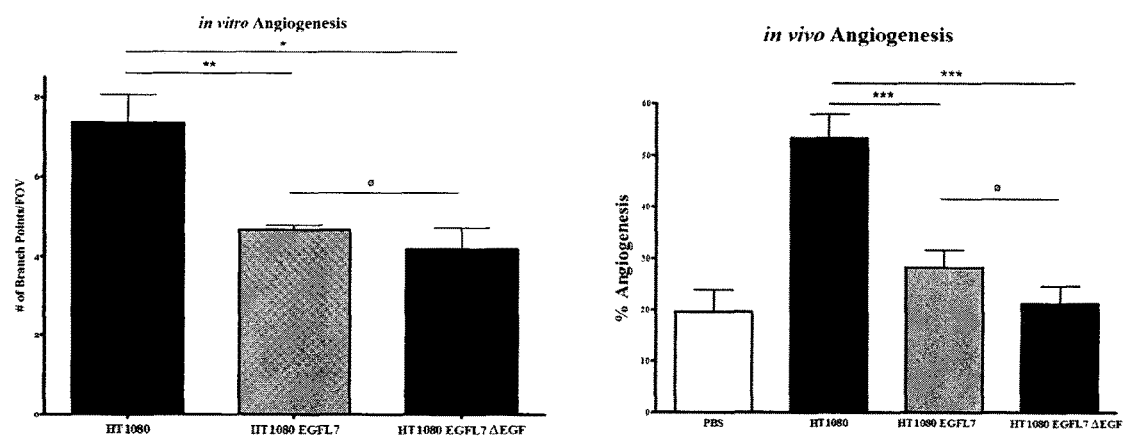
FIG. 6 shows fluorescein-labeled E7-p72 peptide (HMYFLLGH, SEQ ID NO: 5) uptake by HUVECs evaluated by flow cytometry, (a) Western blot analysis showing the knockdown of EGFL7 using a siRNA targeting the exon 5. (b) Flow cytometry analysis of FITC-E7-p72 (FITC-HMY-FLLGH, SEQ ID NO: 5) uptake by cells HUVECs treated with either a negative siRNA (control) or EGFL7 siRNA. (c) Graph showing the average cell fluorescence.

The in vitro angiogenesis assay was also used to determine that the Notch binding domain is not required for the effects of GSLLVHSFQQLG (SEQ ID NO: 6) or HMYFLLGH (SEQ ID NO: 5) (FIG. 6).

Example 4—Use of EGFL7 Interacting Polypeptides for Imaging

Methods:
Cell Uptake Study of FITC-E7-p72 (FITC-HMYFLLGH; SEQ ID NO: 20) and FITC-E7-p72(dAA) (FITC-HMYFLLGH(dAA))

EGFL7 knockdown in human umbilical vein endothelial cells (HUVECs) was achieved using a siRNA targeting the exon 5 of the protein and INTERFERin transfection reagent (HUVECs-si). Wildtype HUVECs and HUVECs-si cells were seeded onto separate wells in a 6-well tissue culture plate to approximately 80% confluency. The cells were incubated overnight in DMEM containing 10% fetal bovine serum and Pen/Strep at 37° C. with 5% $CO_2$. The media in each well were removed and replaced with pre-chilled PBS. FITC-E7-p72 (FITC-HMYFLLGH; SEQ ID NO: 20) was added onto cells to a final concentration of 1 mM and incubated for 1 hour at 4° C. Cells were detached from the well with EDTA, washed three times with PBS, and fixed with 4% formaldehyde. The uptake of FITC-labeled peptides was analyzed by flow cytometry.

Figure 7:
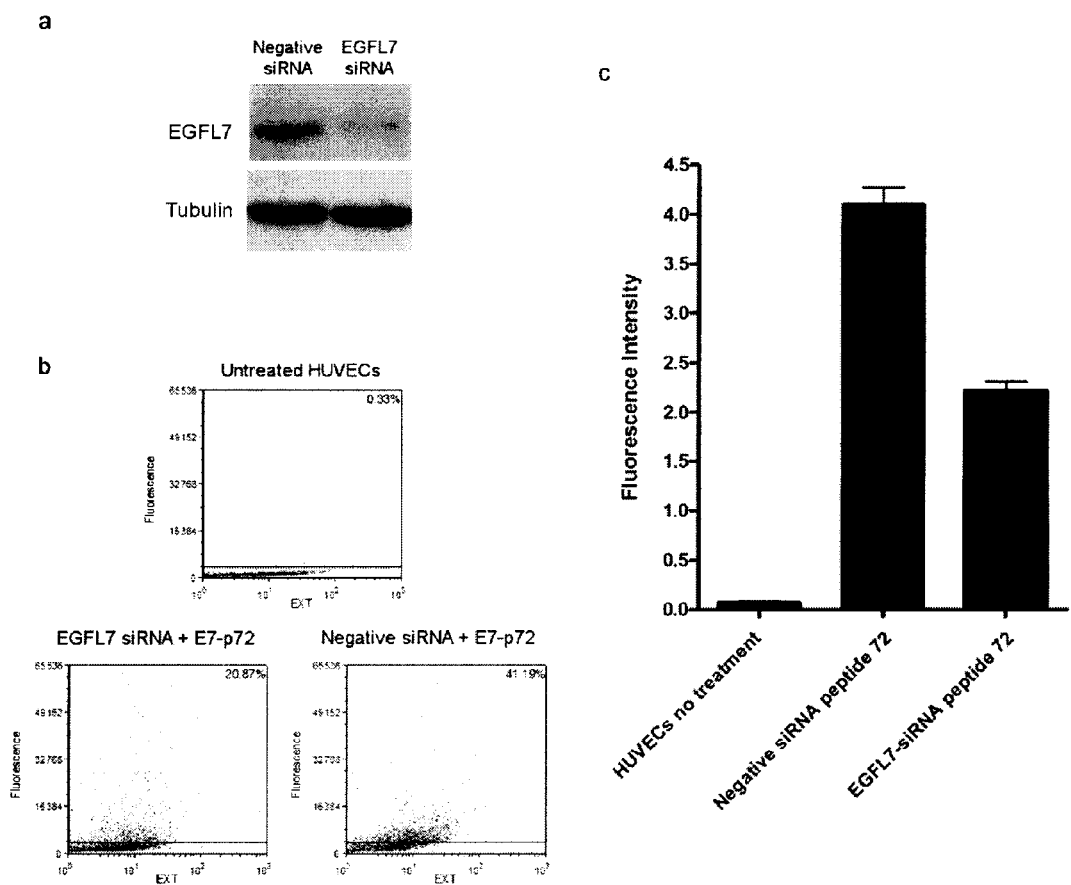
FIG. 7 shows that the uptake of E7-p72 peptide (HMY-FLLGH, SEQ ID NO: 5) in human endothelial cells is dependent on EGFL7 expression, (a) Western blot analysis showing the knockdown of EGFL7 using a siRNA targeting exon 5 of EGFL7. (b) Flow cytometry analysis of FITC-E7-p72 (FITC-HMYFLLGH, SEQ ID NO: 5) uptake by HUVECs treated with either a negative siRNA (control) or EGFL7 siRNA (n=10 000). (c) Graph depicting the average cellular fluorescence from flow cytometry experiment in (b).

Results:

Fluorescein-labeled HMYFLLGH (SEQ ID NO: 5) peptide uptake by HUVECs was evaluated by flow cytometry. Western blot analysis showing the knockdown of EGFL7 using a siRNA targeting the exon 5 is shown in FIG. 7A. Flow cytometry analysis of FITC-labelled HMYFLLGH (SEQ ID NO: 5) uptake by HUVEC cells treated with either a negative siRNA (control) or EGFL7 siRNA is shown in FIG. 7B. FIG. 7C shows a graph of the average cell fluorescence, plotted using GraphPad Prism, version 5.0.

Example 5—Directed In Vivo Angiogenesis Assay (DIVAA)

Methods:

A DIVAA kit was used to assess angiogenesis in 7 week old female Nude mice (Crl:NU-Foxn1nu; Charles River), as per the manufacturer's recommended protocol (Trevigen, Gaithersburg, Md.). Angioreactor tubes were filled with basement membrane extract (BME), BME+50,000 HT1080 cells, or BME+50,000 HT1080+GSLLVHSFQQLG (SEQ ID NO: 6) (LCE71) or HMYFLLGH (SEQ ID NO: 5) (LCE72/E7-p72), and inserted subcutaneously into mice. After 10 days, mice were sacrificed, angioreactors were removed, and angioreactor contents were transferred into a centrifuge tube. Endothelial cells were labelled overnight in a FITC-Lectin solution, and fluorescence was quantified using a plate reader. All experiments involving animals were approved by the Animal Use Subcommittee at the University of Western Ontario (Protocol No. 2008-101).

Figure 9A:
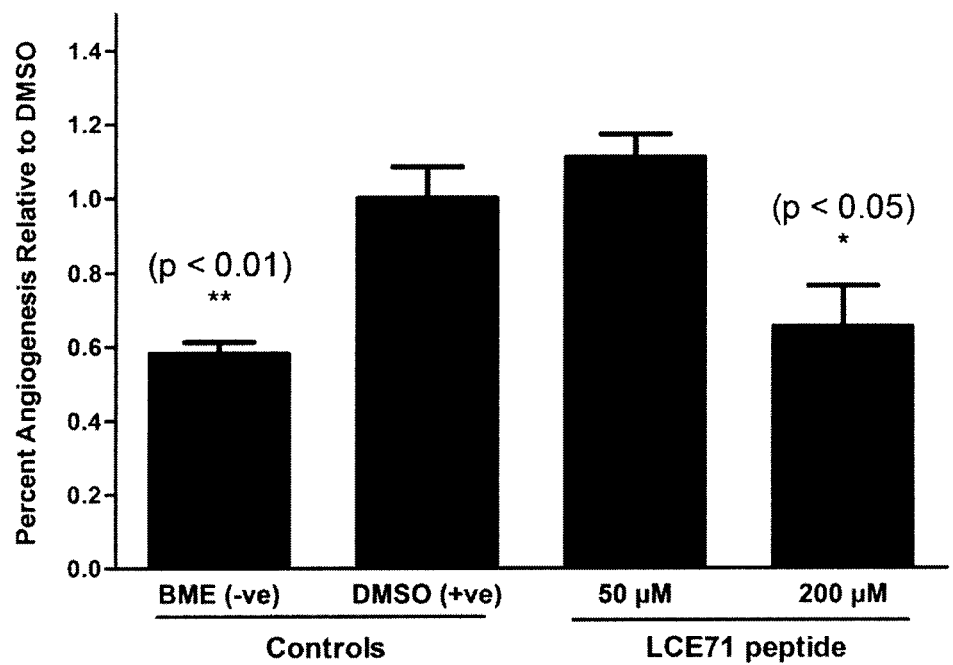
FIG. 9 shows that (A) LCE71 (GSLLVHSFQQLG, SEQ ID NO: 6) and (B) LCE72/E7-p72 (HMYFLLGH, SEQ ID NO: 5) peptides inhibit angiogenesis in mice using the directed in vivo angiogenesis assay (DIVAA). Bar graphs show the percent angiogenesis observed in angioreactor tubes (n=8) from each group. Angioreactors were filled with basement membrane extract (BME). HT1080 cells were added to stimulate angiogenesis. BME (−ve) is a negative control that contained only BME without cells. All statistics were performed using a one-way ANOVA and tukey post hoc test.
Figure 9B:
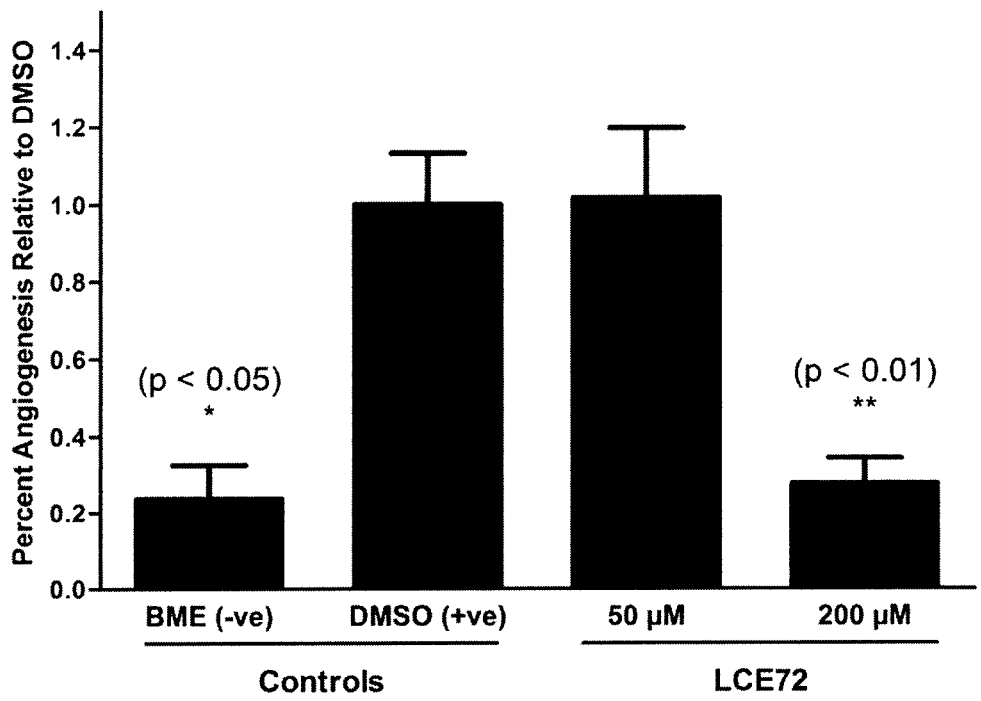

Results:

FIG. 9A shows that 200 µM GSLLVHSFOOLG (SEQ ID NO: 6) was able to inhibit HT1080 cell-mediated angiogenesis in angioreactors filled with basement membrane extract (BME). FIG. 9B shows that 200 µM HMYFLLGH (SEQ ID NO: 5) was able to inhibit HT1080 cell-mediated angiogenesis in angioreactors filled with basement membrane extract (BME).

Example 6—Cell Adhesion Assay and Immunocytochemical Localization of Vinculin in EA.hy926 Endothelial Cells Methods:

For the adhesion assay, EGFL7 siRNA (Sigma, Canada) or scrambled siRNA (negative control) (Sigma, Canada) were used to transfect EA.hy926 endothelial-derived cells. EA.hy926 cells were seeded onto a 6-well plate and transfected with either EGFL7 or scrambled siRNA at a final concentration of 40 nM using INTEFERin transfection reagent (Polyplus transfection). EA.hy926 endothelial-derived cells treated with EGFL7 siRNA or scrambled siRNA (negative control) were detached by treatment with trypsin/EDTA and re-suspended in DMEM containing 1% serum. Cells were plated into 96-well plate and treated with 200 µM of Flag (control), scrambled GSLLVHSFQQLG (SEQ ID NO: 6) peptide for 4 hrs at 37° C. Cells were then washed three times with PBS and fixed with 4% formaldehyde. Cell nuclei were stained with Hoechst (Pierce) and imaged under the EVOS f1 inverted fluorescent microscope (AMG). The number of cells that remained adhered to the plate was determined using by Volocity, version 4.0. All statistics were performed using a one-way ANOVA and Tukey post hoc test.

For the vinculin staining, EA.hy926 cells were plated onto coverslips and treated with 200 µM of scrambled (control) or GSLLVHSFQQLG (SEQ ID NO: 6) peptide for 4 hrs at 37° C. in DMEM containing 1% serum. Cells were then washed three times with PBS and fixed with 4% formaldehyde. Cells were permeabilized with PBS containing 0.2% Triton-X for 5 minutes, and then blocked with 5% goat serum and 1% BSA for 1 hour 25° C. Anti-vinculin primary antibody were added at a 1:500 dilution and incubated for 1 hour at 25° C. Cells were washed three times with PBS and incubated with an Alexa Fluor 594 secondary antibody (Invitrogen, Canada) at a 1:1000 dilution 1 hour 25° C. Cells were washed three times with PBS. Cells were then treated with wheat germ agglutinin (WGA) at a 1:1000 dilution for 10 minutes at room temperature. Cells were washed twice, mounted with ProLong Gold reagent containing DAPI, and imaged under the Zeiss spinning disk confocal microscope. Z-stacked images were captured through each cell.

Figure 10:
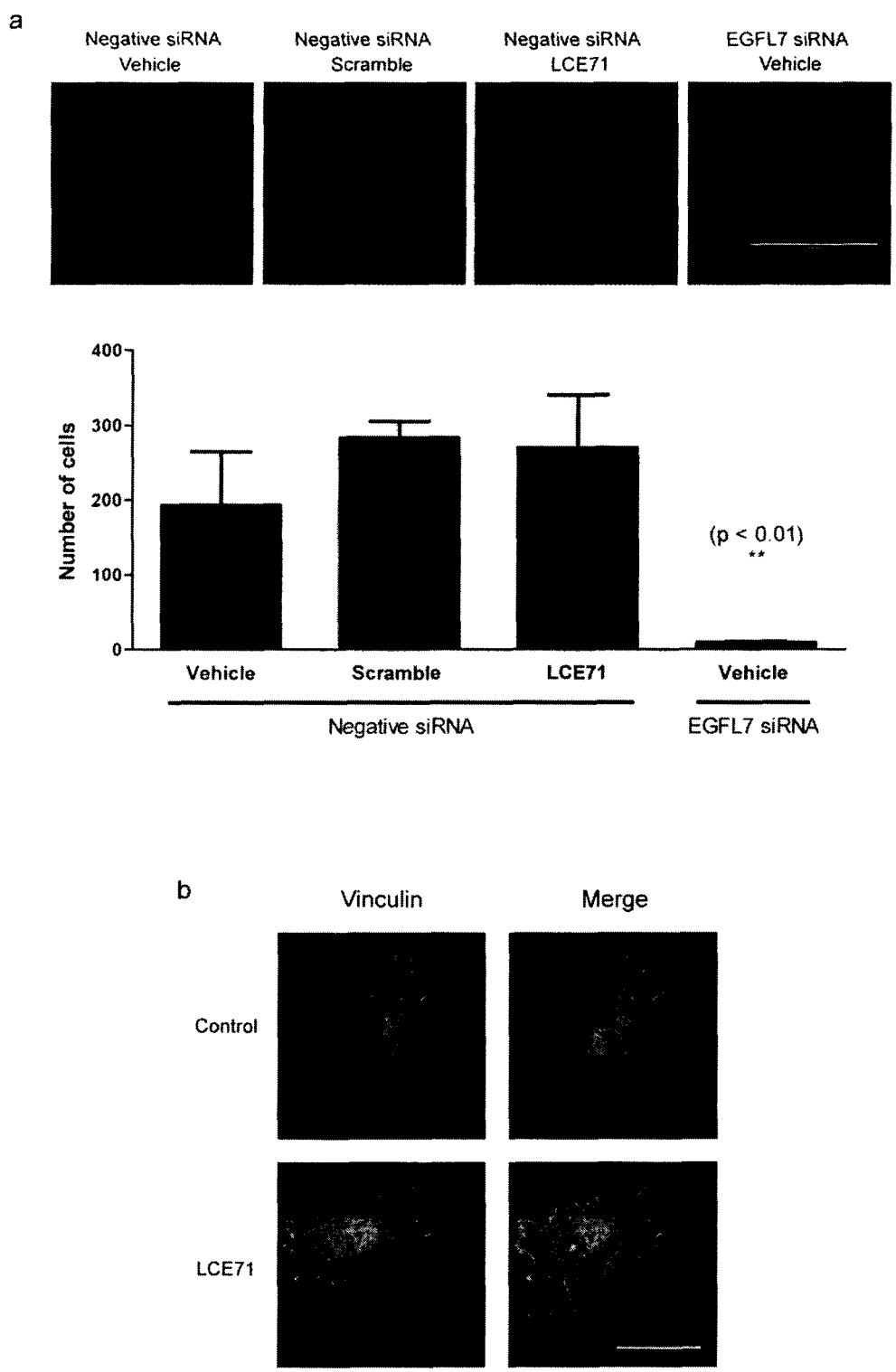
FIG. 10 shows that LCE71 (GSLLVHSFQQLG, SEQ ID NO: 6) does not alter the adherent property of human endothelial cells, (a) Cell adhesion assay showing that LCE71 (200 pM) does not alter the cell adhesion property of EA.hy926 endothelial cells compared to Flag or scramble peptide. Knockdown of EGFL7 in EA.hy926 cells using siRNA significantly decreased cell adhesion ($p<0.01$). Cell nuclei were stained with Hoechst dye, imaged and counted using the Volocity software (version 6.1.2, Improvision). All statistics were performed using a one-way ANOVA and tukey post hoc test, (b) Vinculin staining of EA.hy926 cells showing focal adhesion formation on glass coverslip. Left panel: Vinculin (orange) and DAPI (blue). Right panel: merged images of vinculin (orange), WGA plasma membrane stain (green) and DAPI (blue). Scale bar, 10 pm.

Results:

FIG. 10 shows that GSLLVHSFQQLG (SEQ ID NO: 6) (LCE71) does not alter the adherent property of human endothelial cells. FIG. 10A shows the results of a cell adhesion assay, in which the adhesion of EA.hy926 endothelial cells was shown to be no different when a scrambled siRNA was used on the cells or when 200 µM GSLLVHSFQQLG (SEQ ID NO: 6) (LCE71) was applied to the cells as compared to control cells. On the other hand, when siRNA was used that specifically knocked down EGFL7, cell adhesion was significantly decreased, indicating that EGFL7 is an important mediator involved in cell adhesion. FIG. 10B shows EA.hy926 endothelial cells before and after treatment with GSLLVHSFQQLG (SEQ ID NO: 6) (LCE71) stained with vinculin (orange), DAPI (blue) and WGA plasma membrane stain (green). In both cases, focal adhesion formation on the glass coverslip was observed.

Example 7—Phospho-RTK Profiler Array

Methods:

HUVECs were detached by treatment with trypsin/EDTA and resuspended in EGM. Cells were plated into a T-75 flask and treated with 200 µM of Flag or E7C13 peptide for 4 hrs at 37° C. in EGM. Cells were harvested and lysed in Array Buffer 1 according to the Human Phospho-Receptor Tyrosine Kinase (RTK) Array Kit (R&D systems) manufacturer's guideline. After blocking, each phospho-RTK array membranes were incubated with 100 µg of lysate according to the manufacturer's guidelines. Membranes were washed, and incubated with anti-phospho-HRP. Activated tyrosine kinases were detected by enhanced chemiluminescence (ECL) as per manufacturer's guidelines.

43

Figure 11:
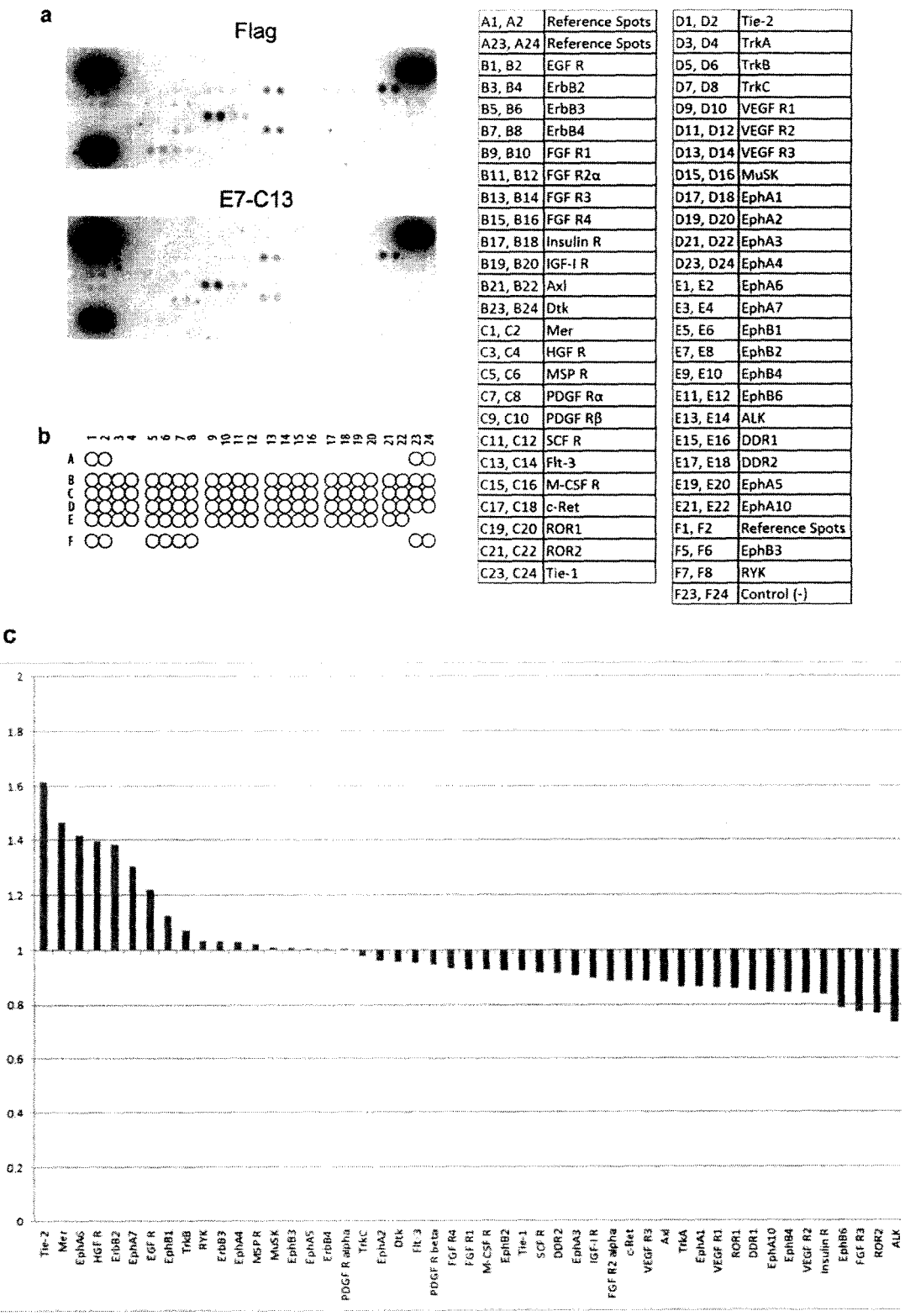
FIG. 11 shows the Profiling RTK activation in HUVECs upon treatment with LCE71 (GSLLVHSFQQLG, SEQ ID NO: 6). (a) Array membranes displaying 49 different anti-human RTK antibodies (R&D systems) incubated with lysates from HUVECs treated with either control Flag or LCE71 (GSLLVHSFQQLG, SEQ ID NO: 6) peptide (200 µM) for 4 hrs. Phosphorylated RTKs were detected by incubation with an anti-phospho-HRP antibody followed by treatment with enhanced chemiluminescence. (b) Phospho-RTK array coordinates (left) and their respective RTKs (right table), (c) Waterfall plot showing the activation profile of RTKs in HUVECs upon treatment with LCE71 (GSLL-VHSFQQLG, SEQ ID NO: 6) peptide. The mean signal intensity of each spot from (a) was quantified using Volocity (version 6.1.2, PerkinElmer). The values obtained from LCE71-treated membrane were normalized to the values obtained from Flag-treated membrane.

Results:

FIG. 11 profiles RTK activation in HUVECs upon treatment with GSLLVHSFQQLG (SEQ ID NO: 6) (LCE71). FIG. 11A shows array membranes displaying 49 different anti-human RTK antibodies incubated with lysates from HUVECs that were either treated with control FLAG peptide or 200 μM GSLLVHSFQQLG (SEQ ID NO: 6) (LCE71) peptide. FIG. 11B shows the array coordinates (left) and their respective RTKs (right table). FIG. 11C is a waterfall plot showing the activation profile of RTKs in HUVECs after treatment with GSLLVHSFQQLG (SEQ ID NO: 6) peptide. It can be seen that the phosphorylation of several RTKs was increased, such as Tie-2, Mer and fibroblast growth factor receptor 3 (FGFR3) and that the phosphorylation of several other RTKs was decreased, such as anaplastic lymphoma kinase (ALK), vascular endothelial growth factor receptor (VEGF R) and Axl.

Example 8—Immunoprecipitation of Phosphotyrosines

Methods:

HUVECs were grown in a T-75 flask and treated with 200 μM of Flag or E7C13 peptide for 4 hrs at 37° C. in EGM. Cells were washed with PBS, and lysed in RIPA buffer (50 mM Tris-HCl, 150 mM NaCl, 2 mM EDTA, 1 mM NaF, 1 mM PMSF, 1% NP40, 0.1% sodium deoxycholate, 0.1% SDS). Cell lysate was collected, and the protein concentration was determined using a BCA protein assay. An aliquot of lysate from each sample was set aside for western blot analysis. Each lysate was pre-cleared by incubating the lysate with 30 μL of washed protein A/G beads for 1 hour at 4° C. on a rotator. Pre-cleared lysate was collected by centrifugation (12,000×g for 5 seconds) and incubated with 3 μL of 4G10 anti-phospho antibody (Millipore) for 2 hours at 4° C. Washed protein A/G beads (30 μL) were added to each sample and incubated for 2 hour at 4° C. on a rotator. Lysate was collected by centrifugation (12,000×g for 5 seconds) and set aside for western blot analysis. Immunocomplexes were washed five times using wash buffer (50 mM Tris-HCl, 150 mM NaCl, 2 mM EDTA, 1 mM NaF, 1% NP40) and analyzed by SDS-PAGE and western blot. Protein samples were run on an 8% gel and transferred onto PVDF membrane (Bio-Rad). Detection of immunoprecipitated protein was done with the anti-Axl antibody (R&D Systems), and anti-VEGFR-1 antibody (Sigma, Canada).

44

Results:

FIG. 12 confirms the results of the profiler array and shows that phosphorylation of Axl and VEGFR1 RTKs in HUVECs is decreased upon treatment with GSLLVHSFQQLG (SEQ ID NO: 6) (LCE71). FIG. 12A shows western blots of HUVECs that were treated with either control Flag peptide or 200 μM LCE71 (GSLLVHSFQQLG; SEQ ID NO: 6) peptide for 4 hours. Immunoprecipitation was performed using the 4G10 anti-phospho antibody coupled onto Protein A/G agarose. Western blot analyses were performed using the anti-Axl, anti-VEGFR1 and anti-GAPDH antibody. FIG. 12B is a bar graph showing the mean signal intensity of each band obtained from western blot shown in FIG. 12A.

Example 9—Synthesis of DOTA-EGFL7 Peptides

1. Synthesis of DOTA-LCE71 (DOTA-GSLLVHSFQQLG; SEQ ID NO: 6)/DOTA-LCE72 (DOTA-HMYFLLGH; SEQ ID NO: 5)

The peptide was synthesized by classical procedures for solid-phase synthesis with the resin (Rink-Amide-MBNA) (Scheme 1):

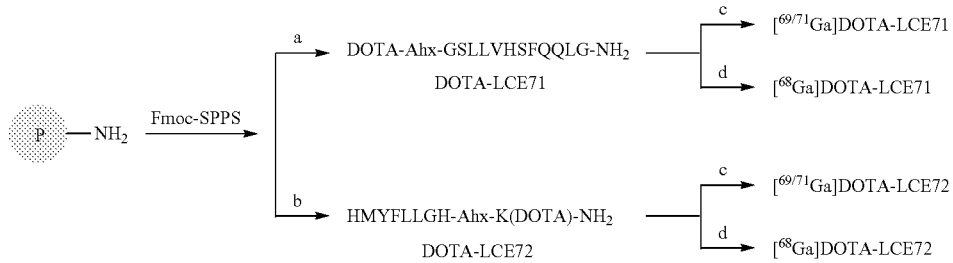

Scheme 1. synthesis of [Ga]DOTA-LCE71 and [Ga]DOTA-LCE72

Reaction condition: a) (tBu)₃DOTA, HCTU, DIPEA, DMF; b) TFA/H₂O/Tis (95%/2.5%/2.5%); c) $^{69/71}$GaCl₃, NaOAc/HOAc pH = 4.5; d) TFA/DCM (2%); e) piperidine/DMF (20%)

Fmoc-deprotection: the removal of Fmoc protecting group from resin or N-terminal of peptide by piperidine/DMF (40%, 1.2 mL) twice. DMF was used to wash resin for 6 times.

b) Peptide coupling condition: The coupling reaction was performed by Fmoc-amino acid and HCTU in DMF (4 eq) and DIPEA (8 eq) in DMF for 5 min at 75° C. and washed with DMF. DOTA(t-Bu)₃ and Fmoc-histidine was coupled at room temperature for 1 h.

c) Cleavage of peptides from resin: the peptide was finally treated with cleavage cocktail of TFA/H2O/TIS 95%/2.5%/2.5% for 6 h.

d) Cleavage of mtt protecting group from peptide with Fmoc-protected N-terminal on resin. The mixture (TFA/TIS/DCM: 2%/5%/93%) was used to cleave mtt group for 2 mL×6.

e) Peptide purification: After cleavage of peptide from resin, the raw peptide was diluted with cool tert-butylmethyl ether and precipitated out by centrifuge. The raw peptide was purified on HPLC and lyophilized to get white solid (35 mg, 9.7% for DOTA-LCE71; 32 mg, 9.8% for DOTA-LCE72).

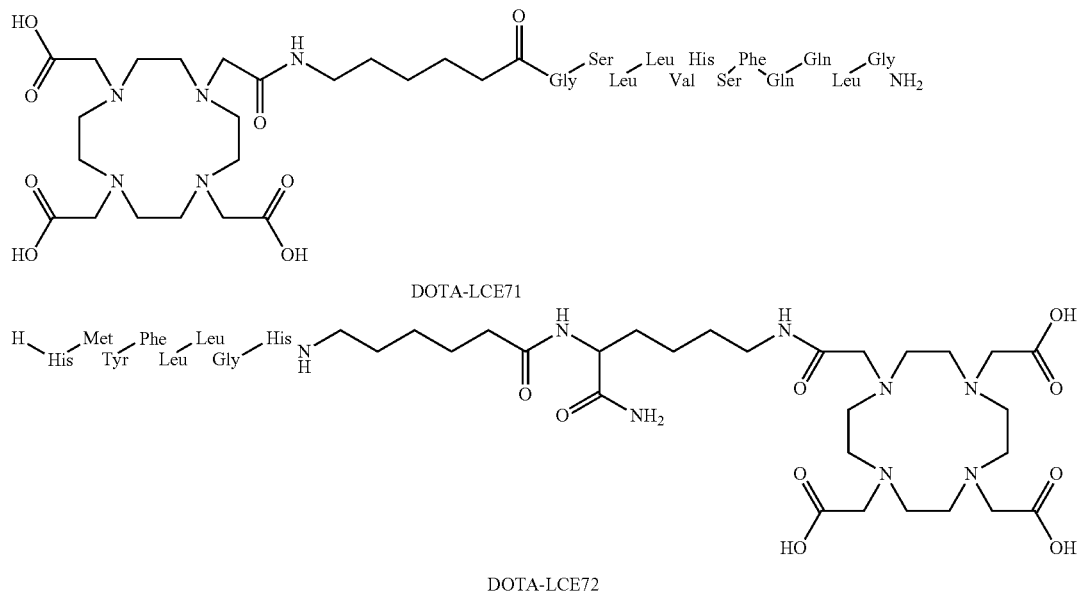

DOTA-LCE71

DOTA-LCE72

2. Synthesis of [$^{69/71}$Ga]DOTA-LCE71/LCE72 (-GSLL-VHSFQQLG/HMYFLLGH; SEQ ID NO: 6/5)

DOTA-LCE71/DOTA-LCE72 (10 mg) was dissolved in NaOAc/HOAc (pH=5, 0.1 M), GaCl3 (5 mg) was added and heated for 70° C. for 30 min. the reaction mixture was purified on HPLC and lyophilized to get white solid. (3 mg for [$^{69/71}$Ga]DOTA-LCE71; 2 mg for [$^{69/71}$Ga]DOTA-LCE72).

3. Radiosynthesis of [$^{68}$Ga]DOTA-LCE71/LCE72 (-GSLL-VHSFQQLG/HMYFLLGH; SEQ ID NO: 6/5)

The [$^{68}$Ga]DOTA-LCE71/LCE72 was automatically synthesized by Eckert&Ziegler module as described in Scheme 2:

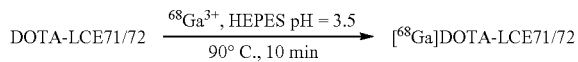

DOTA-LCE71/72 $\xrightarrow[90° C., 10 min]{^{68}Ga^{3+}, HEPES pH = 3.5}$ [$^{68}$Ga]DOTA-LCE71/72

Figure 13:
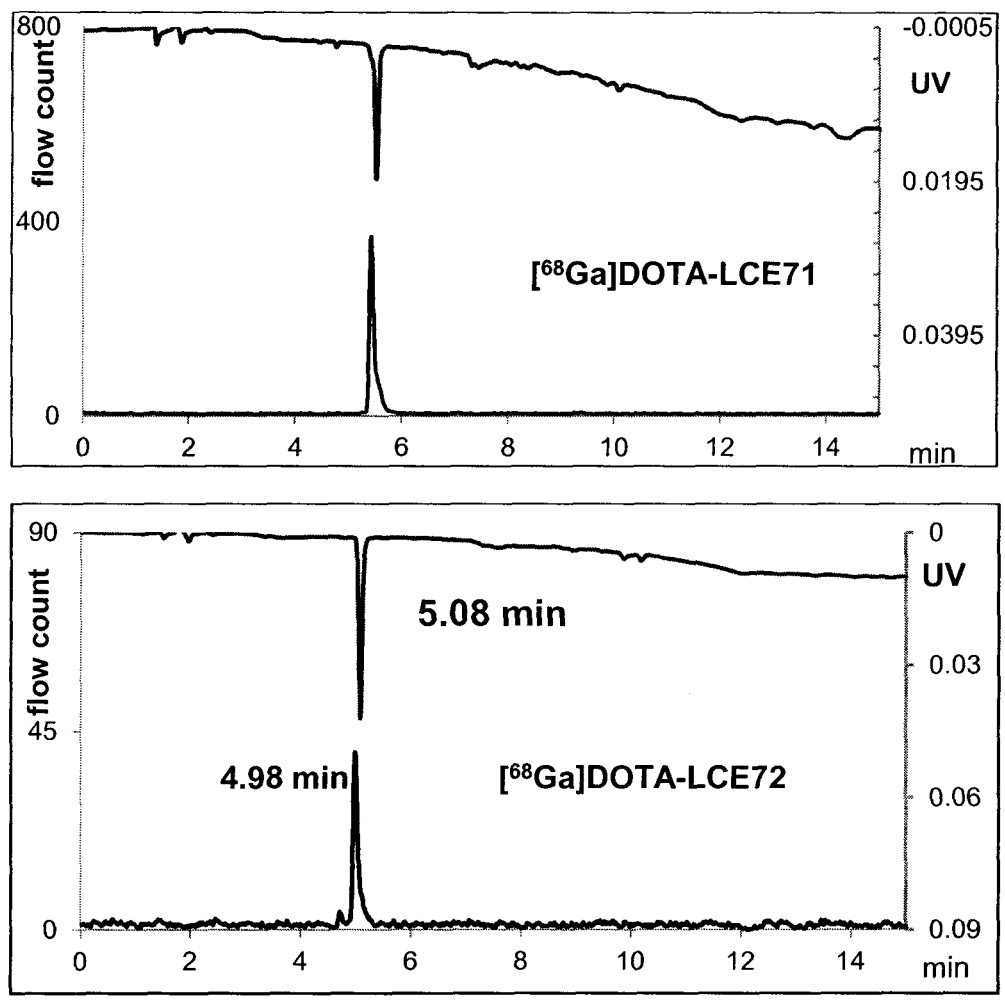
FIG. 13 shows the radiochemical purity of synthesized [$^{68}$Ga]DOTA-LCE71/LCE72 ([$^{68}$Ga]DOTA-GSLLVHS-FQQLG/HMYFLLGH, SEQ ID NO: 6 and SEQ ID NO: 5, respectively). HPLC condition: mobile phase: acetonitrile/H20, gradient 10/90 to 90/10 (v/v) with TFA 0.1%, 10 min, flow rate: 1.5 mL/min, Sunfire RP analytic column; chromatograph: flow count(black); UV(254 nm, red).

10 μg of precursor (DOTA-LCE71/LCE72) in 100 uL of HEPES buffer (1M, pH=3.5) was mixed with $^{68}$Ga$^{3+}$ in N2 solution (300 μL). The reaction vial was heated at 90° C. for 10 min. The reaction vial was cooled down to RT and trapped in Sep-Pak C-18 cartridge. Ethanol was used to wash out the product from Sep-Pak C-18 cartridge. The radiochemical yield was 81% for [$^{68}$Ga]DOTA-LCE71, 53% for [$^{68}$Ga]DOTA-LCE72. The specific activity was 3.3 GBq/μmol for [$^{68}$Ga]DOTA-LCE71 and 9.4 GBq/μmol for [$^{68}$Ga]DOTA-LCE72. The radiochemical purity was measured on analytical HPLC (FIG. 13).

Example 10—Tumour Reduction Study

We will evaluate the potential of EGFL7 interacting peptides to treat solid tumours in nude mice that have been established with different fibrosarcoma, human prostate, and breast cancer cell lines. We will compare the efficacy of these peptides to that of control or scramble peptides. We will then translate the application of these promising anti-angiogenic peptide candidates into the clinic to be used to treat cancer in patients.

Figure 14:
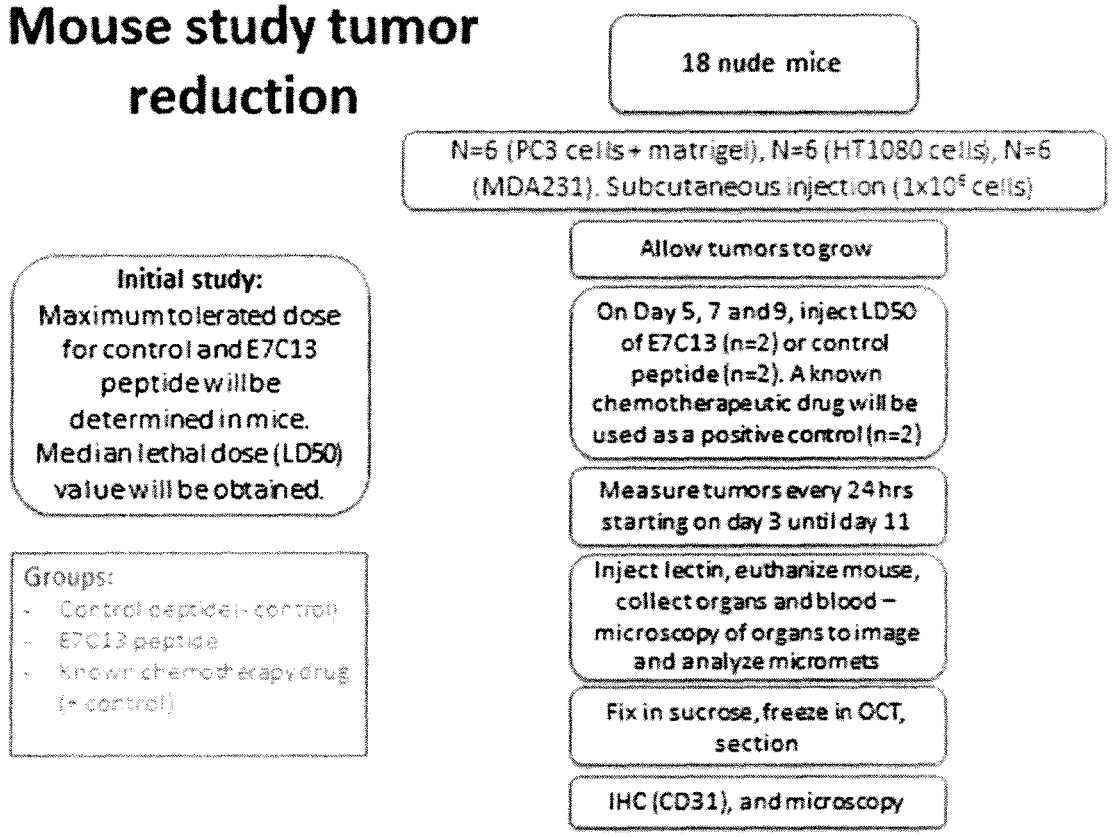
FIG. 14 shows a flow chart for evaluating the potential of EGFL7 interacting peptides to treat solid tumours in nude mice that have been established with different fibrosarcoma, human prostate, and breast cancer cell lines.

Protocol:

The protocol is generally shown in the flowchart of FIG. 14. Nude mice will be anaesthetized and will receive subcutaneous injection of prostate cancer (PC3), breast cancer (MDA231), or fibrosarcoma (HT1080) cells into the lower back of one side of the mouse to induce primary disease.

A dose curve will be generated first to determine the amount of EGFL7 interacting peptide that can be tolerated by the animals.

Tumours will be allowed to grow to approximately 15 mm$^3$.

Based on the dose curve, the animals will receive tail vein injection of EGFL7 interacting peptide (E7-p72/HMYFLLGH (SEQ ID NO: 5) or LCE71/GSLLVHSFQQLG (SEQ ID NO: 6)) or control peptide. In addition, we will also administer EGFL7 interacting peptide in combination with Avastin to evaluate whether treatment with the peptide can provide synergistic therapeutic benefit compared to treatment with Avastin alone.

Animals will be euthanized and the tumours will be resected, fixed, frozen, and sectioned for histological analysis.

Organs will also be collected for biodistribution studies.

Expected Results:

We expect that mice treated with E7-p72 (HMYFLLGH; SEQ ID NO: 5) or LCE71 (GSLLVHSFQQLG; SEQ ID NO: 6) will have reduced tumour size and prolonged life span compared to mice treated with control peptide. We also expect that anti-EGFL7 treatment using these peptides will provide additive therapeutic benefit compared to treatment with Avastin alone. In our histological analysis, we expect to see fewer vessels associated with tumours in mice that have been treated with EGFL7 interacting peptide due to a predictable decrease in angiogenesis, based upon the examples described above.

The above disclosure generally describes the present invention. Although specific terms have been employed herein, such terms are intended in a descriptive sense and not for purposes of limitation.

All publications, patents and patent applications are herein incorporated by reference in their entirety to the same extent as if each individual publication, patent or patent application was specifically and individually indicated to be incorporated by reference in its entirety.

Although exemplary embodiments of the invention have been described herein in detail, it will be understood by those skilled in the art that variations may be made thereto without departing from the spirit of the invention or the scope of the appended claims.

The invention claimed is:

1. A polypeptide that interacts with a domain of EGFL7, wherein said polypeptide comprises at least about 90% identity to the sequence HMYFLLGH (SEQ ID NO: 5), GSLLVHSFQQLG (SEQ ID NO: 6), DPYDHEFR (SEQ ID NO: 7), AYYEEAYE (SEQ ID NO: 8), RYVDHEDW (SEQ ID NO: 9), EWELHAEE (SEQ ID NO: 10), SQSSMYPS (SEQ ID NO: 11), RYQLHHPR (SEQ ID NO: 12), WYKLHPTM (SEQ ID NO: 13), or a biologically active variant thereof, or wherein said polypeptide comprises the sequence KLQLVLAPLHSLAS (SEQ ID NO: 14), or RSPGLAPARPRYA (SEQ ID NO: 15).

2. The polypeptide of claim 1, wherein the polypeptide interacts with the C-terminal domain of EGFL7, or wherein the polypeptide interacts with EGFL7 outside of the Notch binding domain of EGFL7.

3. The polypeptide of claim 1, wherein said polypeptide comprises the sequence HMYFLLGH (SEQ ID NO: 5), GSLLVHSFQQLG (SEQ ID NO: 6), DPYDHEFR (SEQ ID NO: 7), AYYEEAYE (SEQ ID NO: 8), RYVDHEDW (SEQ ID NO: 9), EWELHAEE (SEQ ID NO: 10), SQSSMYPS (SEQ ID NO: 11), RYQLHHPR (SEQ ID NO: 12), or WYKLHPTM (SEQ ID NO: 13).

4. The polypeptide of claim 1, wherein said polypeptide comprises at least about 95% identity to the sequence HMYFLLGH (SEQ ID NO: 5), GSLLVHSFQQLG (SEQ ID NO: 6), DPYDHEFR (SEQ ID NO: 7), AYYEEAYE (SEQ ID NO: 8), RYVDHEDW (SEQ ID NO: 9), EWELHAEE (SEQ ID NO: 10), SQSSMYPS (SEQ ID NO: 11), RYQLHHPR (SEQ ID NO: 12), WYKLHPTM (SEQ ID NO: 13), or a biologically active variant thereof.

5. The polypeptide of claim 4, wherein said polypeptide comprises at least about 99% identity to the sequence HMYFLLGH (SEQ ID NO: 5), GSLLVHSFQQLG (SEQ ID NO: 6), DPYDHEFR (SEQ ID NO: 7), AYYEEAYE (SEQ ID NO: 8), RYVDHEDW (SEQ ID NO: 9), EWELHAEE (SEQ ID NO: 10), SQSSMYPS (SEQ ID NO: 11), RYQLHHPR (SEQ ID NO: 12), WYKLHPTM (SEQ ID NO: 13), or a biologically active variant thereof.

6. The polypeptide of claim 1, comprising a conservative amino acid substitution.

7. The polypeptide of claim 1, wherein said polypeptide comprises the sequence KLQLVLAPLHSLAS (SEQ ID NO: 14) or RSPGLAPARPRYA (SEQ ID NO: 15).

8. The polypeptide of claim 1, wherein said polypeptide comprises from about 8 to about 300 amino acid residues.

9. The polypeptide of claim 8, wherein said polypeptide comprises from about 8 to about 250 amino acid residues, from about 8 to about 200 amino acid residues, from about 8 to about 100 amino acid residues, from about 8 to about 50 amino acid residues, from about 8 to about 30 amino acid residues, from about 8 to about 20 amino acid residues, from about 8 to about 16 amino acid residues, from about 8 to about 12 amino acid residues, or from about 12 to about 16 amino acid residues.

10. The polypeptide of claim 1, wherein said polypeptide consists of the sequence HMYFLLGH (SEQ ID NO: 5), GSLLVHSFQQLG (SEQ ID NO: 6), DPYDHEFR (SEQ ID NO: 7), AYYEEAYE (SEQ ID NO: 8), RYVDHEDW (SEQ ID NO: 9), EWELHAEE (SEQ ID NO: 10), SQSSMYPS (SEQ ID NO: 11), RYQLHHPR (SEQ ID NO: 12), WYKLHPTM (SEQ ID NO: 13), KLQLVLAPLHSLAS (SEQ ID NO: 14), or RSPGLAPARPRYA (SEQ ID NO: 15).

11. The polypeptide of claim 1, wherein the polypeptide is HMYFLLGH (SEQ ID NO: 5) or GSLLVHSFQQLG (SEQ ID NO: 6).

12. The polypeptide of claim 1, wherein said polypeptide comprises a detectable label.

13. The polypeptide of claim 12, wherein said label is gadolinium.

14. The polypeptide of claim 1, wherein said polypeptide is coupled to a pharmaceutical agent for targeted delivery of the pharmaceutical agent to a site containing expressed EGFL7 within a subject.

15. The polypeptide of claim 14, wherein said pharmaceutical agent is an anti-VEGF antibody.

16. The polypeptide of claim 14 wherein said pharmaceutical agent is coupled to said polypeptide via a nanoparticle.

17. A polypeptide comprising at least 90% identity to the sequence HMYFLLGH (SEQ ID NO: 5), or a biologically active variant thereof.

18. The polypeptide of claim 17, wherein said polypeptide comprises a conservative amino acid substitution.

19. A polypeptide comprising at least 90% identity to the sequence GSLLVHSFQQLG (SEQ ID NO: 6), or a biologically active variant thereof, wherein said polypeptide comprises from about 12 to about 250 amino acid residues.

20. The polypeptide of claim 19, wherein said polypeptide comprises a conservative amino acid substitution.

* * * * *

UNITED STATES PATENT AND TRADEMARK OFFICE
CERTIFICATE OF CORRECTION

PATENT NO. : 9,789,213 B2
APPLICATION NO. : 14/388678
DATED : October 17, 2017
INVENTOR(S) : Lewis et al.

Page 1 of 2

It is certified that error appears in the above-identified patent and that said Letters Patent is hereby corrected as shown below:

On the Title Page

Item (56) References Cited, OTHER PUBLICATIONS: Please correct "PCT/CA2013/000261" to read -- PCT/CA2013/000251 --

In the Specification

Column 7, Line 64: Please correct "(200 NM)" to read -- (200 µm) --

Column 25, Line 30: Please correct "ΔGT11" to read -- λgt11 --

Column 37, Line 63: Please correct "pH 7.9" to read -- pH 7·9 --

Column 39, Lines 1-20: Please replace TABLE 1 with

Table 1. EGFL7 interacting polypeptides.

| LCE# | Sequence | Purity | MS calc | MS expt |
|---|---|---|---|---|
| 74 | Ac-KLQLVLAPLHSLAS-NH2<br>SEQ ID NO: 16 | >98% | $[M+2H]^{2+} = 767.0$ | 768.2 |
| 83 | H-CKLQLVLAPLHSLAS-NH2<br>SEQ ID NO: 17 | >90% | $[M+2H]^{2+} = 797.0$ | 796.8 |
| 136 | H-HMYFLLGH-NH2<br>SEQ ID NO: 5 | >99% | $[M+2H]^{2+} = 1016.5$ | 1016.61 |
| 137 | H-HMYFLLGH(Ahx)(LysDOTA)-NH2<br>SEQ ID NO: 18 | >95% | $[M+2H]^{2+} = 822.9$ | 824.7 |
| 171 | H-hMYFLLGh-NH2<br>SEQ ID NO: 19 | >95% | $[M+2H]^{2+} = 508.8$ | 508.9 |
| 172 | H-hMYFLLGh(Ahx)(LysFITC)-NH2<br>SEQ ID NO: 20 | >95% | $[M+2H]^{2+} = 824.4$ | 824.3 |
| 177 | H-HMYFLLGH(Ahx)(LysN3)-NH2<br>SEQ ID NO: 21 | >99% | $[M+H]^{+} = 1283.7$ | 1284.1 |
| 185 | H-hMYFLLGH-NH2<br>SEQ ID NO: 22 | >99% | $[M+H]^{+} = 1016.5$ | 1016.6 |
| 231 | H-H(DabN3)YFLLGH-NH2<br>SEQ ID NO: 23 | >99% | $[M+H]^{+} = 1012.2$ | 1011.8 |

Signed and Sealed this
Fourteenth Day of August, 2018

Andrei Iancu
*Director of the United States Patent and Trademark Office*

| | | | | |
|---|---|---|---|---|
| 232 | H-h(DabN3)YFLLGH-NH2 SEQ ID NO: 24 | >99% | [M+H]⁺= 1012.2 | 1011.8 |
| 233 | H-H(DabN3)YFLLGh-NH2 SEQ ID NO: 25 | >99% | [M+H]⁺= 1012.2 | 1011.7 |
| 234 | H-h(DabN3)YFLLGh-NH2 SEQ ID NO: 26 | >99% | [M+H]⁺= 1012.2 | 1011.7 |
| 235 | H-H(Nle)YFLLGH-NH2 SEQ ID NO: 27 | >99% | [M+H]⁺= 999.2 | 998.8 |
| 236 | H-h(Nle)YFLLGH-NH2 SEQ ID NO: 28 | >99% | [M+H]⁺= 999.2 | 998.7 |
| 237 | H-H(Nle)YFLLGh-NH2 SEQ ID NO: 29 | >98% | [M+H]⁺= 999.2 | 998.8 |
| 238 | H-h(Nle)YFLLGh-NH2 SEQ ID NO: 30 | >99% | [M+H]⁺= 999.2 | 998.8 |

SEQUENCE LISTING

```
<160> NUMBER OF SEQ ID NOS: 32

<210> SEQ ID NO 1
<211> LENGTH: 273
<212> TYPE: PRT
<213> ORGANISM: Homo sapiens

<400> SEQUENCE: 1

Met Arg Gly Ser Gln Glu Val Leu Leu Met Trp Leu Leu Val Leu Ala
1               5                   10                  15

Val Gly Gly Thr Glu His Ala Tyr Arg Pro Gly Arg Arg Val Cys Ala
                20                  25                  30

Val Arg Ala His Gly Asp Pro Val Ser Glu Ser Phe Val Gln Arg Val
            35                  40                  45

Tyr Gln Pro Phe Leu Thr Thr Cys Asp Gly His Arg Ala Cys Ser Thr
        50                  55                  60

Tyr Arg Thr Ile Tyr Arg Thr Ala Tyr Arg Ser Pro Gly Leu Ala
65                  70                  75                  80

Pro Ala Arg Pro Arg Tyr Ala Cys Cys Pro Gly Trp Lys Arg Thr Ser
                85                  90                  95

Gly Leu Pro Gly Ala Cys Gly Ala Ala Ile Cys Gln Pro Pro Cys Arg
            100                 105                 110

Asn Gly Gly Ser Cys Val Gln Pro Gly Arg Cys Arg Cys Pro Ala Gly
        115                 120                 125

Trp Arg Gly Asp Thr Cys Gln Ser Asp Val Asp Glu Cys Ser Ala Arg
130                 135                 140

Arg Gly Gly Cys Pro Gln Arg Cys Ile Asn Thr Ala Gly Ser Tyr Trp
145                 150                 155                 160

Cys Gln Cys Trp Glu Gly His Ser Leu Ser Ala Asp Gly Thr Leu Cys
                165                 170                 175

Val Pro Lys Gly Gly Pro Pro Arg Val Ala Pro Asn Pro Thr Gly Val
            180                 185                 190

Asp Ser Ala Met Lys Glu Glu Val Gln Arg Leu Gln Ser Arg Val Asp
        195                 200                 205

Leu Leu Glu Glu Lys Leu Gln Leu Val Leu Ala Pro Leu His Ser Leu
    210                 215                 220

Ala Ser Gln Ala Leu Glu His Gly Leu Pro Asp Pro Gly Ser Leu Leu
225                 230                 235                 240

Val His Ser Phe Gln Gln Leu Gly Arg Ile Asp Ser Leu Ser Glu Gln
                245                 250                 255

Ile Ser Phe Leu Glu Glu Gln Leu Gly Ser Cys Ser Cys Lys Lys Asp
            260                 265                 270

Ser

<210> SEQ ID NO 2
<211> LENGTH: 278
<212> TYPE: PRT
<213> ORGANISM: Mus musculus

<400> SEQUENCE: 2

Met Gln Thr Met Trp Gly Ser Gly Glu Leu Leu Val Ala Trp Phe Leu
```

-continued

```
            1               5                   10                  15
          Val Leu Ala Ala Asp Gly Thr Thr Glu His Val Tyr Arg Pro Ser Arg
                          20                  25                  30

Arg Val Cys Thr Val Gly Ile Ser Gly Gly Ser Ile Leu Glu Thr Phe
                          35                  40                  45

Val Gln Arg Val Tyr Gln Pro Tyr Leu Thr Thr Cys Asp Gly His Arg
           50                  55                  60

Ala Cys Ser Thr Tyr Arg Thr Ile Tyr Arg Thr Ala Tyr Arg Arg Ser
           65                  70                  75                  80

Pro Gly Val Thr Pro Ala Arg Pro Arg Tyr Ala Cys Cys Pro Gly Trp
                          85                  90                  95

Lys Arg Thr Ser Gly Leu Pro Gly Ala Cys Gly Ala Ala Ile Cys Gln
                         100                 105                 110

Pro Pro Cys Gly Asn Gly Gly Ser Cys Ile Arg Pro Gly His Cys Arg
                         115                 120                 125

Cys Pro Val Gly Trp Gln Gly Asp Thr Cys Gln Thr Asp Val Asp Glu
                         130                 135                 140

Cys Ser Thr Gly Glu Ala Ser Cys Pro Gln Arg Cys Val Asn Thr Val
          145                 150                 155                 160

Gly Ser Tyr Trp Cys Gln Gly Trp Glu Gly Gln Ser Pro Ser Ala Asp
                         165                 170                 175

Gly Thr Arg Cys Leu Ser Lys Glu Gly Pro Ser Pro Val Ala Pro Asn
                         180                 185                 190

Pro Thr Ala Gly Val Asp Ser Met Ala Arg Glu Glu Val Tyr Arg Leu
                         195                 200                 205

Gln Ala Arg Val Asp Val Leu Glu Gln Lys Leu Gln Leu Val Leu Ala
                         210                 215                 220

Pro Leu His Ser Leu Ala Ser Arg Ser Thr Glu His Gly Leu Gln Asp
          225                 230                 235                 240

Pro Gly Ser Leu Leu Ala His Ser Phe Gln Gln Leu Asp Arg Ile Asp
                         245                 250                 255

Ser Leu Ser Glu Gln Val Ser Phe Leu Glu Glu His Leu Gly Ser Cys
                         260                 265                 270

Ser Cys Lys Lys Asp Leu
                         275

<210> SEQ ID NO 3
<211> LENGTH: 280
<212> TYPE: PRT
<213> ORGANISM: Xenopus laevis

<400> SEQUENCE: 3

Met Trp Lys Val Ser Cys Leu Val Thr Gly Tyr Leu Leu Ile Leu Ala
           1               5                  10                  15

Val Thr Ser Ala Ala Ala Asp His Leu Tyr Arg Thr Gly Arg Arg Ile
                          20                  25                  30

Cys Ser Ala Asp Gly His Pro Gly Thr Val Ser Val Thr Gln Ser Phe
                          35                  40                  45

Val Gln Pro Val His Ser Pro Ile Met Thr Leu Cys Glu Gly His Arg
           50                  55                  60

Ile Cys Ser Thr Tyr Arg Thr Thr Tyr Lys Val Ser Tyr Arg Gln Val
           65                  70                  75                  80

Ser Arg Lys Thr Ser Phe Pro Leu Tyr Ser Cys Cys Pro Gly Trp Arg
                          85                  90                  95
```

Arg Ile Gly Ala Gln Thr His Ser Cys Gly Gln Ala Leu Cys Arg Leu
            100                 105                 110

Gln Cys Gln Asn Gly Gly Thr Cys Val Ser Ser Asn Lys Cys Glu Cys
            115                 120                 125

Pro Ala Gly Trp Arg Gly Ile His Cys Gln Met Asp Val Asp Glu Cys
            130                 135                 140

Ser Asp Gly Thr His Gln Cys Ser Gln Ala Cys Ile Asn Ser Ala Gly
145                 150                 155                 160

Ser Phe Ser Cys Glu Cys Leu Glu Gly Tyr Arg Leu Met Ala Asp Gly
                    165                 170                 175

Lys Thr Cys Arg Lys Val Pro Ala Pro Thr Val Pro Pro Ala Ser Pro
            180                 185                 190

Thr Ser Val Gln Glu Ser Gly Ile Pro His Ser Val Lys Glu Glu Met
            195                 200                 205

Ala Glu Leu Arg Ser Lys Ile Asp Val Leu Glu Gln Lys Leu His Leu
            210                 215                 220

Leu Leu Thr Pro Phe Gln Gly Leu Thr Thr Phe Ser Pro Asp Asp Ala
225                 230                 235                 240

Ala Asp Pro Ile Ala Leu Leu Thr Arg Ser Leu Gln Gln Leu Asp Arg
                    245                 250                 255

Ile Asp Ser Leu Ser Glu Gln Ile Ser Phe Leu Glu Glu Arg Leu Glu
            260                 265                 270

Thr Cys Ser Cys Lys Thr Glu Leu
            275                 280

<210> SEQ ID NO 4
<211> LENGTH: 277
<212> TYPE: PRT
<213> ORGANISM: Danio rerio

<400> SEQUENCE: 4

Met Tyr Thr Ala Leu Leu Leu Ser Ser Leu Phe Leu Leu His Val
1               5                   10                  15

Thr Cys Thr Pro Gln Thr His Ser His His Gly Arg Arg Val Cys Val
            20                  25                  30

Gly Asp Val Trp Ser Arg Arg Val Ser Tyr Ser Thr Glu Ser Phe Leu
            35                  40                  45

Gln Pro Val His Lys Pro Tyr Ile Thr Met Cys Gln Asn His Arg Met
            50                  55                  60

Cys Ser Thr Tyr Lys Thr Ile Tyr Lys Val Ser Tyr Arg Gln Val Thr
65                  70                  75                  80

Arg Ala Ala Pro Asn Leu Gln Ile Tyr Pro Glu Cys Cys Pro Gly Trp
                    85                  90                  95

Arg Arg Met His Ser His Asn Cys Asn Gln Ala Val Cys Glu Gln Ser
            100                 105                 110

Cys Ala Asn Gly Gly Ser Cys Val Arg Pro Asn His Cys Ala Cys Leu
            115                 120                 125

Arg Gly Trp Thr Gly Arg Phe Cys Gln Ile Asp Val Asp Glu Cys Lys
            130                 135                 140

Glu Ala Gln His Cys Ser Gln Lys Cys Val Asn Thr Leu Gly Ser Phe
145                 150                 155                 160

Gln Cys Val Cys Glu Glu Gly Phe Ser Leu Asp Glu Asp Lys Val Thr
                    165                 170                 175

Cys Ser Lys Asn Pro Ala Ser Ser Arg Asn Thr Gly Gly Gly Leu Gly
            180                 185                 190

```
Leu Val Glu Asn Val Thr Glu Val Gln Ile Leu Lys Asn Arg Val
        195                 200                 205

Glu Leu Leu Glu Gln Lys Leu Glu Met Val Leu Ala Pro Phe Thr Thr
    210                 215                 220

Leu Leu Pro Leu Asp Gly Ala Gly Asp Thr Asn Ser Phe Leu Ser Glu
225                 230                 235                 240

Arg Thr Asn Phe Leu Ser His Ser Leu Gln Gln Leu Asp Arg Ile Glu
                245                 250                 255

Ser Leu Ser Glu Gln Val Gly Phe Leu Glu Glu Arg Ile Gly Ala Cys
            260                 265                 270

Gly Cys Gln Glu Asn
        275

<210> SEQ ID NO 5
<211> LENGTH: 8
<212> TYPE: PRT
<213> ORGANISM: Artificial Sequence
<220> FEATURE:
<223> OTHER INFORMATION: EGFL7 interacting peptide

<400> SEQUENCE: 5

His Met Tyr Phe Leu Leu Gly His
1               5

<210> SEQ ID NO 6
<211> LENGTH: 12
<212> TYPE: PRT
<213> ORGANISM: Artificial Sequence
<220> FEATURE:
<223> OTHER INFORMATION: EGFL7 interacting peptide

<400> SEQUENCE: 6

Gly Ser Leu Leu Val His Ser Phe Gln Gln Leu Gly
1               5                   10

<210> SEQ ID NO 7
<211> LENGTH: 8
<212> TYPE: PRT
<213> ORGANISM: Artificial Sequence
<220> FEATURE:
<223> OTHER INFORMATION: EGFL7 interacting peptide

<400> SEQUENCE: 7

Asp Pro Tyr Asp His Glu Phe Arg
1               5

<210> SEQ ID NO 8
<211> LENGTH: 8
<212> TYPE: PRT
<213> ORGANISM: Artificial Sequence
<220> FEATURE:
<223> OTHER INFORMATION: EGFL7 interacting peptide

<400> SEQUENCE: 8

Ala Tyr Tyr Glu Glu Ala Tyr Glu
1               5

<210> SEQ ID NO 9
<211> LENGTH: 8
<212> TYPE: PRT
<213> ORGANISM: Artificial Sequence
<220> FEATURE:
<223> OTHER INFORMATION: EGFL7 interacting peptide
```

```
<400> SEQUENCE: 9

Arg Tyr Val Asp His Glu Asp Trp
1               5

<210> SEQ ID NO 10
<211> LENGTH: 8
<212> TYPE: PRT
<213> ORGANISM: Artificial Sequence
<220> FEATURE:
<223> OTHER INFORMATION: EGFL7 interacting peptide

<400> SEQUENCE: 10

Glu Trp Glu Leu His Ala Glu Glu
1               5

<210> SEQ ID NO 11
<211> LENGTH: 8
<212> TYPE: PRT
<213> ORGANISM: Artificial Sequence
<220> FEATURE:
<223> OTHER INFORMATION: EGFL7 interacting peptide

<400> SEQUENCE: 11

Ser Gln Ser Ser Met Tyr Pro Ser
1               5

<210> SEQ ID NO 12
<211> LENGTH: 8
<212> TYPE: PRT
<213> ORGANISM: Artificial Sequence
<220> FEATURE:
<223> OTHER INFORMATION: EGFL7 interacting peptide

<400> SEQUENCE: 12

Arg Tyr Gln Leu His His Pro Arg
1               5

<210> SEQ ID NO 13
<211> LENGTH: 8
<212> TYPE: PRT
<213> ORGANISM: Artificial Sequence
<220> FEATURE:
<223> OTHER INFORMATION: EGFL7 interacting peptide

<400> SEQUENCE: 13

Trp Tyr Lys Leu His Pro Thr Met
1               5

<210> SEQ ID NO 14
<211> LENGTH: 14
<212> TYPE: PRT
<213> ORGANISM: Artificial Sequence
<220> FEATURE:
<223> OTHER INFORMATION: EGFL7 interacting peptide

<400> SEQUENCE: 14

Lys Leu Gln Leu Val Leu Ala Pro Leu His Ser Leu Ala Ser
1               5                   10

<210> SEQ ID NO 15
<211> LENGTH: 13
<212> TYPE: PRT
<213> ORGANISM: Artificial Sequence
<220> FEATURE:
<223> OTHER INFORMATION: EGFL7 interacting peptide

<400> SEQUENCE: 15
```

```
Arg Ser Pro Gly Leu Ala Pro Ala Arg Pro Arg Tyr Ala
1               5                   10

<210> SEQ ID NO 16
<211> LENGTH: 14
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (1)..(1)
<223> OTHER INFORMATION: ACETYLATION

<400> SEQUENCE: 16

Lys Leu Gln Leu Val Leu Ala Pro Leu His Ser Leu Ala Ser
1               5                   10

<210> SEQ ID NO 17
<211> LENGTH: 15
<212> TYPE: PRT
<213> ORGANISM: Artificial Sequence
<220> FEATURE:
<223> OTHER INFORMATION: EGFL7 interacting peptide

<400> SEQUENCE: 17

Cys Lys Leu Gln Leu Val Leu Ala Pro Leu His Ser Leu Ala Ser
1               5                   10                  15

<210> SEQ ID NO 18
<211> LENGTH: 10
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (9)..(9)
<223> OTHER INFORMATION: Xaa is Acp
<220> FEATURE:
<221> NAME/KEY: MISC_FEATURE
<222> LOCATION: (10)..(10)
<223> OTHER INFORMATION: DOTA-modified residue

<400> SEQUENCE: 18

His Met Tyr Phe Leu Leu Gly His Xaa Lys
1               5                   10

<210> SEQ ID NO 19
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (8)..(8)
<223> OTHER INFORMATION: D-amino acid residue

<400> SEQUENCE: 19

His Met Tyr Phe Leu Leu Gly His
1               5

<210> SEQ ID NO 20
<211> LENGTH: 10
```

```
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (8)..(8)
<223> OTHER INFORMATION: D-amino acid residue
<220> FEATURE:
<221> NAME/KEY: MISC_FEATURE
<222> LOCATION: (9)..(9)
<223> OTHER INFORMATION: Xaa is Acp
<220> FEATURE:
<221> NAME/KEY: MISC_FEATURE
<222> LOCATION: (10)..(10)
<223> OTHER INFORMATION: FITC-modified residue

<400> SEQUENCE: 20

His Met Tyr Phe Leu Leu Gly His Xaa Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (9)..(9)
<223> OTHER INFORMATION: Xaa is Acp
<220> FEATURE:
<221> NAME/KEY: MISC_FEATURE
<222> LOCATION: (10)..(10)
<223> OTHER INFORMATION: N3-modified residue

<400> SEQUENCE: 21

His Met Tyr Phe Leu Leu Gly His Xaa Lys
1               5                   10

<210> SEQ ID NO 22
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (1)..(1)
<223> OTHER INFORMATION: D-amino acid residue

<400> SEQUENCE: 22

His Met Tyr Phe Leu Leu Gly His
1               5

<210> SEQ ID NO 23
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (2)..(2)
<223> OTHER INFORMATION: Xaa is Dbu
<220> FEATURE:
<221> NAME/KEY: MISC_FEATURE
<222> LOCATION: (2)..(2)
<223> OTHER INFORMATION: N3-modified residue
```

```
<400> SEQUENCE: 23

His Xaa Tyr Phe Leu Leu Gly His
1               5

<210> SEQ ID NO 24
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (2)..(2)
<223> OTHER INFORMATION: Xaa is Dbu
<220> FEATURE:
<221> NAME/KEY: MISC_FEATURE
<222> LOCATION: (2)..(2)
<223> OTHER INFORMATION: N3-modified residue

<400> SEQUENCE: 24

His Xaa Tyr Phe Leu Leu Gly His
1               5

<210> SEQ ID NO 25
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (2)..(2)
<223> OTHER INFORMATION: Xaa is Dbu
<220> FEATURE:
<221> NAME/KEY: MISC_FEATURE
<222> LOCATION: (2)..(2)
<223> OTHER INFORMATION: N3-modified residue
<220> FEATURE:
<221> NAME/KEY: MISC_FEATURE
<222> LOCATION: (8)..(8)
<223> OTHER INFORMATION: D-amino acid residue

<400> SEQUENCE: 25

His Xaa Tyr Phe Leu Leu Gly His
1               5

<210> SEQ ID NO 26
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (2)..(2)
<223> OTHER INFORMATION: Xaa is Dbu
<220> FEATURE:
<221> NAME/KEY: MISC_FEATURE
<222> LOCATION: (2)..(2)
<223> OTHER INFORMATION: N3-modified residue
<220> FEATURE:
<221> NAME/KEY: MISC_FEATURE
<222> LOCATION: (8)..(8)
<223> OTHER INFORMATION: D-amino acid residue
```

<400> SEQUENCE: 26

His Xaa Tyr Phe Leu Leu Gly His
1               5

<210> SEQ ID NO 27
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (2)..(2)
<223> OTHER INFORMATION: Xaa is Nle
<220> FEATURE:
<221> NAME/KEY: MISC_FEATURE
<222> LOCATION: (2)..(2)
<223> OTHER INFORMATION: N3-modified residue

<400> SEQUENCE: 27

His Xaa Tyr Phe Leu Leu Gly His
1               5

<210> SEQ ID NO 28
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (2)..(2)
<223> OTHER INFORMATION: Xaa is Nle
<220> FEATURE:
<221> NAME/KEY: MISC_FEATURE
<222> LOCATION: (2)..(2)
<223> OTHER INFORMATION: N3-modified residue

<400> SEQUENCE: 28

His Xaa Tyr Phe Leu Leu Gly His
1               5

<210> SEQ ID NO 29
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (2)..(2)
<223> OTHER INFORMATION: Xaa is Nle
<220> FEATURE:
<221> NAME/KEY: MISC_FEATURE
<222> LOCATION: (2)..(2)
<223> OTHER INFORMATION: N3-modified residue
<220> FEATURE:
<221> NAME/KEY: MISC_FEATURE
<222> LOCATION: (8)..(8)
<223> OTHER INFORMATION: D-amino acid residue

<400> SEQUENCE: 29

His Xaa Tyr Phe Leu Leu Gly His
1               5

<210> SEQ ID NO 30

```
<211> LENGTH: 8
<212> TYPE: PRT
<213> ORGANISM: Artificial Sequence
<220> FEATURE:
<223> OTHER INFORMATION: EGFL7 interacting peptide
<220> FEATURE:
<221> NAME/KEY: MISC_FEATURE
<222> LOCATION: (1)..(1)
<223> OTHER INFORMATION: D-amino acid residue
<220> FEATURE:
<221> NAME/KEY: MISC_FEATURE
<222> LOCATION: (2)..(2)
<223> OTHER INFORMATION: Xaa is Nle
<220> FEATURE:
<221> NAME/KEY: MISC_FEATURE
<222> LOCATION: (2)..(2)
<223> OTHER INFORMATION: N3-modified residue
<220> FEATURE:
<221> NAME/KEY: MISC_FEATURE
<222> LOCATION: (8)..(8)
<223> OTHER INFORMATION: D-amino acid residue

<400> SEQUENCE: 30

His Xaa Tyr Phe Leu Leu Gly His
1               5

<210> SEQ ID NO 31
<211> LENGTH: 25
<212> TYPE: DNA
<213> ORGANISM: Artificial Sequence
<220> FEATURE:
<223> OTHER INFORMATION: PCR Primer

<400> SEQUENCE: 31
caccatgagg ggctctcagg aggtg                                          25

<210> SEQ ID NO 32
<211> LENGTH: 25
<212> TYPE: DNA
<213> ORGANISM: Artificial Sequence
<220> FEATURE:
<223> OTHER INFORMATION: PCR Primer

<400> SEQUENCE: 32
ctacgagtct ttcttgcagg agcag                                          25
```